(12) United States Patent
Snyder

(10) Patent No.: US 10,549,081 B2
(45) Date of Patent: Feb. 4, 2020

(54) DRUG DELIVERY DEVICE AND METHODS HAVING A RETAINING MEMBER

(71) Applicant: Warsaw Orthopedic, Inc., Warsaw, IN (US)

(72) Inventor: Lloyd M. Snyder, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 227 days.

(21) Appl. No.: 15/190,861

(22) Filed: Jun. 23, 2016

(65) Prior Publication Data
US 2017/0368323 A1 Dec. 28, 2017

(51) Int. Cl.
A61M 37/00 (2006.01)
A61K 9/00 (2006.01)
A61M 5/28 (2006.01)

(52) U.S. Cl.
CPC ....... *A61M 37/0069* (2013.01); *A61K 9/0024* (2013.01); *A61M 5/28* (2013.01)

(58) Field of Classification Search
CPC ............ A61M 37/0069; A61M 31/007; A61K 9/0024
See application file for complete search history.

(56) References Cited

U.S. PATENT DOCUMENTS

| 797,183 A | 10/1904 | Davis |
| 1,881,854 A | 10/1932 | Muir |
| 2,502,909 A | 4/1950 | Wick et al. |
| 3,016,895 A | 1/1962 | Sein |

(Continued)

FOREIGN PATENT DOCUMENTS

| DE | 1955059 | 2/1967 |
| DE | 19640670 | 5/1998 |

(Continued)

OTHER PUBLICATIONS

Abd-Elsayed et al., "A Double-Blind Randomized Controlled Trial Comparing Epidural Clonidine vs Bupivacaine for Pain Control During and After Lower Abdominal Surgery", The Ochsner Journal, 2015, vol. 15, pp. 133-142.

(Continued)

*Primary Examiner* — Emily L Schmidt
(74) *Attorney, Agent, or Firm* — Knobbe, Martens & Olson & Bear, LLP

(57) ABSTRACT

A device for delivering a drug depot into a patient via a cannula is provided. The device includes a housing with a coupling mechanism. A drug cartridge is positioned within the housing and includes a cartridge depot channel having an occluding device that includes a ramp and a plateau. The occluding device occludes the cartridge depot channel to prevent the drug depot from moving beyond the occluding device without force applied to the drug depot sufficient to deflect the occluding device an amount to allow the drug depot to move beyond the occluding device. The drug cartridge includes an alignment boss with an end channel coaxial with the cartridge depot channel. A push rod is slidably receivable in the housing and the drug cartridge to move the drug depot beyond the occluding device, into the cartridge depot channel, through the cannula and into the patient.

20 Claims, 8 Drawing Sheets

(56) References Cited

U.S. PATENT DOCUMENTS

| | | |
|---|---|---|
| 3,520,299 A | 7/1970 | Tapper et al. |
| 3,620,216 A | 11/1971 | Szymanski |
| 4,044,989 A | 8/1977 | Basel et al. |
| 4,069,825 A | 1/1978 | Akiyama |
| 4,105,030 A | 8/1978 | Kercso |
| 4,164,560 A | 8/1979 | Folkman et al. |
| D262,156 S | 12/1981 | Grubelnig |
| 4,344,431 A | 8/1982 | Yolles |
| 4,346,709 A | 8/1982 | Schmitt |
| 4,427,015 A | 1/1984 | Redeaux |
| 4,451,253 A | 5/1984 | Harman |
| 4,516,593 A | 5/1985 | Muto |
| 4,525,156 A | 6/1985 | Benusa et al. |
| 4,559,054 A | 12/1985 | Bruck |
| 4,576,591 A | 3/1986 | Kaye et al. |
| 4,624,255 A | 11/1986 | Schenck et al. |
| 4,624,848 A | 11/1986 | Lee |
| 4,700,692 A | 10/1987 | Baumgartner |
| 4,742,054 A | 5/1988 | Naftchi |
| 4,774,091 A | 9/1988 | Yamahira et al. |
| 4,781,695 A | 11/1988 | Dalton |
| 4,791,939 A | 12/1988 | Maillard |
| 4,819,684 A | 4/1989 | Zaugg et al. |
| 4,820,267 A | 4/1989 | Harman |
| 4,820,284 A | 4/1989 | Hauri |
| 4,855,335 A | 8/1989 | Neperud |
| 4,863,457 A | 9/1989 | Lee |
| 4,871,094 A | 10/1989 | Gall et al. |
| 4,892,538 A | 1/1990 | Patrick et al. |
| 4,900,304 A | 2/1990 | Fujioka et al. |
| 4,909,250 A | 3/1990 | Smith |
| 5,024,655 A | 6/1991 | Freeman et al. |
| 5,024,841 A | 6/1991 | Chu et al. |
| 5,131,401 A | 7/1992 | Westenskow et al. |
| D328,644 S | 8/1992 | Pericic |
| 5,163,904 A | 11/1992 | Lampropoulos et al. |
| 5,180,716 A | 1/1993 | Yaksh et al. |
| 5,183,470 A | 2/1993 | Wettermann |
| 5,196,015 A | 3/1993 | Neubardt |
| 5,207,678 A | 5/1993 | Harms et al. |
| 5,212,162 A | 5/1993 | Missel et al. |
| 5,236,426 A | 8/1993 | Schottes et al. |
| 5,284,479 A | 2/1994 | De Jong |
| 5,312,351 A | 5/1994 | Gerrone |
| 5,330,768 A | 7/1994 | Park et al. |
| 5,337,735 A | 8/1994 | Salerno |
| D353,668 S | 12/1994 | Banks |
| 5,391,081 A | 2/1995 | Lampotang et al. |
| D362,064 S | 9/1995 | Smick |
| 5,449,351 A | 9/1995 | Zohmann |
| 5,466,219 A | 11/1995 | Lynn et al. |
| 5,474,558 A | 12/1995 | Neubardt |
| 5,487,739 A | 1/1996 | Aebischer et al. |
| 5,514,101 A | 5/1996 | Schulz et al. |
| 5,520,660 A | 5/1996 | Loos et al. |
| 5,522,844 A | 6/1996 | Johnson |
| D373,823 S | 9/1996 | Baldwin |
| 5,571,882 A | 11/1996 | Velter |
| 5,622,940 A | 4/1997 | Ostroff et al. |
| 5,626,838 A | 5/1997 | Cavanaugh, Jr. |
| 5,633,002 A | 5/1997 | Stricker et al. |
| 5,694,920 A | 12/1997 | Abrams et al. |
| 5,725,508 A | 3/1998 | Chanoch et al. |
| 5,733,572 A | 3/1998 | Unger et al. |
| 5,752,930 A | 5/1998 | Rise et al. |
| 5,756,127 A | 5/1998 | Grisoni et al. |
| 5,759,583 A | 6/1998 | Iwamoto et al. |
| 5,772,671 A | 6/1998 | Harmon |
| 5,829,589 A | 11/1998 | Nguyen et al. |
| 5,830,130 A | 11/1998 | Janzen et al. |
| 5,834,001 A | 11/1998 | Dionne et al. |
| 5,868,789 A | 2/1999 | Huebner |
| 5,902,273 A | 5/1999 | Yang et al. |
| 5,928,130 A | 7/1999 | Schmidt |
| 5,928,158 A | 7/1999 | Aristides |
| 5,942,241 A | 8/1999 | Chasin et al. |
| 5,980,927 A | 11/1999 | Nelson et al. |
| 6,001,386 A | 12/1999 | Ashton et al. |
| 6,007,843 A | 12/1999 | Drizen et al. |
| 6,015,557 A | 1/2000 | Tobinick et al. |
| 6,036,978 A | 3/2000 | Gombotz et al. |
| 6,063,057 A | 5/2000 | Choh |
| 6,069,129 A | 5/2000 | Sandberg et al. |
| 6,083,534 A | 7/2000 | Wallach et al. |
| 6,086,614 A | 7/2000 | Mumme |
| 6,102,844 A | 8/2000 | Ravins et al. |
| 6,132,420 A | 10/2000 | Dionne et al. |
| 6,179,862 B1 | 1/2001 | Sawhney |
| 6,190,350 B1 | 2/2001 | Davis et al. |
| 6,193,692 B1 | 2/2001 | Harris et al. |
| 6,203,813 B1 | 3/2001 | Gooberman |
| 6,214,370 B1 | 4/2001 | Nelson et al. |
| 6,235,289 B1 | 5/2001 | Aoki et al. |
| 6,242,004 B1 | 6/2001 | Rault |
| 6,248,345 B1 | 6/2001 | Goldenheim et al. |
| 6,273,877 B1 | 8/2001 | West et al. |
| 6,277,969 B1 | 8/2001 | Le et al. |
| 6,287,588 B1 | 9/2001 | Shih et al. |
| 6,298,256 B1 | 10/2001 | Meyer |
| 6,326,020 B1 | 12/2001 | Kohane et al. |
| 6,331,311 B1 | 12/2001 | Brodbeck et al. |
| 6,391,005 B1 | 5/2002 | Lum et al. |
| 6,413,245 B1 | 7/2002 | Yaacobi et al. |
| 6,428,804 B1 | 8/2002 | Suzuki et al. |
| 6,450,937 B1 | 9/2002 | Mercereau et al. |
| 6,461,631 B1 | 10/2002 | Dunn et al. |
| 6,471,688 B1 | 10/2002 | Harper et al. |
| 6,478,776 B1 | 11/2002 | Rosenman et al. |
| 6,497,729 B1 | 12/2002 | Moussy et al. |
| 6,524,607 B1 | 2/2003 | Goldenheim et al. |
| 6,530,934 B1 | 3/2003 | Jacobsen et al. |
| 6,531,154 B1 | 3/2003 | Mathiowitz et al. |
| 6,534,081 B2 | 3/2003 | Goldenheim et al. |
| 6,551,290 B1 | 4/2003 | Elsberry et al. |
| 6,554,778 B1 | 4/2003 | Fleming |
| 6,565,541 B2 | 5/2003 | Sharp |
| 6,571,125 B2 | 5/2003 | Thompson |
| 6,582,441 B1 | 6/2003 | He et al. |
| 6,589,549 B2 | 7/2003 | Shih et al. |
| 6,594,880 B2 | 7/2003 | Elsberry |
| 6,616,946 B1 | 9/2003 | Meier et al. |
| 6,630,155 B1 | 10/2003 | Chandrashekar et al. |
| 6,632,457 B1 | 10/2003 | Sawhney |
| 6,652,883 B2 | 11/2003 | Goupil et al. |
| 6,673,333 B1 | 1/2004 | Meade et al. |
| 6,676,971 B2 | 1/2004 | Goupil et al. |
| 6,710,126 B1 | 3/2004 | Hirt et al. |
| 6,723,741 B2 | 4/2004 | Jeon et al. |
| 6,723,814 B2 | 4/2004 | Meier et al. |
| 6,735,475 B1 | 5/2004 | Whitehurst et al. |
| 6,756,058 B2 | 7/2004 | Brubaker et al. |
| 6,773,714 B2 | 8/2004 | Dunn et al. |
| 6,869,426 B2 | 3/2005 | Ganem |
| 6,916,308 B2 | 7/2005 | Dixon et al. |
| 6,921,541 B2 | 7/2005 | Chasin et al. |
| 6,936,270 B2 | 8/2005 | Watson et al. |
| 6,971,998 B2 | 12/2005 | Rosenman et al. |
| 6,974,462 B2 | 12/2005 | Sater |
| 6,982,089 B2 | 1/2006 | Tobinick |
| 6,993,375 B2 | 1/2006 | Burbank et al. |
| 7,001,892 B1 | 2/2006 | Chmielewski et al. |
| 7,012,106 B2 | 3/2006 | Yuan et al. |
| 7,018,384 B2 | 3/2006 | Skakoon |
| 7,070,583 B1 | 7/2006 | Higuchi et al. |
| 7,070,809 B2 | 7/2006 | Goupil et al. |
| 7,081,123 B2 | 7/2006 | Merboth et al. |
| 7,108,153 B2 | 9/2006 | Wood |
| 7,144,412 B2 | 12/2006 | Wolf et al. |
| 7,166,570 B2 | 1/2007 | Hunter et al. |
| 7,204,826 B2 | 4/2007 | Tremaglio et al. |
| 7,212,865 B2 | 5/2007 | Cory |
| 7,215,426 B2 | 5/2007 | Tsuyuki et al. |
| 7,220,281 B2 | 5/2007 | Lambrecht et al. |
| 7,223,289 B2 | 5/2007 | Trieu et al. |

(56) References Cited

U.S. PATENT DOCUMENTS

| | | |
|---|---|---|
| 7,229,441 B2 | 6/2007 | Trieu et al. |
| 7,235,043 B2 | 6/2007 | Gellman et al. |
| 7,252,651 B2 | 8/2007 | Haider et al. |
| 7,252,685 B2 | 8/2007 | Bindseil et al. |
| 7,276,477 B2 | 10/2007 | Osslund et al. |
| 7,287,983 B2 | 10/2007 | Ilan |
| 7,302,960 B2 | 12/2007 | Patzer |
| 7,317,091 B2 | 1/2008 | Lazar et al. |
| 7,318,840 B2 | 1/2008 | McKay |
| D561,896 S | 2/2008 | Jones |
| 7,329,259 B2 | 2/2008 | Cragg |
| 7,344,716 B2 | 3/2008 | Di Mauro et al. |
| 7,355,008 B2 | 4/2008 | Stavenhagen et al. |
| 7,357,792 B2 | 4/2008 | Newton et al. |
| 7,361,168 B2 | 4/2008 | Makower et al. |
| 7,367,978 B2 | 5/2008 | Drewry et al. |
| D571,463 S | 6/2008 | Chesnin |
| 7,400,930 B2 | 7/2008 | Sharkey et al. |
| 7,585,280 B2 | 9/2009 | Wilson et al. |
| 7,618,370 B2 | 11/2009 | Choi et al. |
| D606,190 S | 12/2009 | Pruitt |
| 7,637,279 B2 | 12/2009 | Amley et al. |
| 7,700,100 B2 | 4/2010 | Johnson et al. |
| D616,095 S | 5/2010 | Kim |
| 7,727,954 B2 | 6/2010 | McKay |
| 7,741,273 B2 | 6/2010 | McKay |
| D624,653 S | 9/2010 | Boillat |
| 7,798,988 B2 | 9/2010 | Aubert et al. |
| D630,733 S | 1/2011 | Ahlgren |
| 7,955,301 B1 | 6/2011 | McKay |
| 8,029,478 B2 | 10/2011 | Zanella |
| 8,084,582 B2 | 12/2011 | Dahiyat et al. |
| 8,088,119 B2 | 1/2012 | Saal et al. |
| 8,092,424 B2 | 1/2012 | Mueller et al. |
| 8,221,358 B2 | 7/2012 | McKay |
| 8,246,571 B2 | 8/2012 | Simonton et al. |
| 8,267,895 B2 | 9/2012 | McKay |
| 8,337,453 B2 | 12/2012 | Lind |
| 8,357,388 B2 | 1/2013 | McKay |
| 8,481,064 B2 | 7/2013 | McKay |
| 8,485,180 B2 | 7/2013 | Smutney et al. |
| 8,585,655 B2 | 11/2013 | Bierman |
| 8,608,705 B2 | 12/2013 | Peters et al. |
| 8,702,677 B2 | 4/2014 | Simonton et al. |
| 8,715,223 B2 | 5/2014 | McKay |
| D711,542 S | 8/2014 | Pierson |
| 8,834,412 B2 | 9/2014 | Painchaud et al. |
| D715,929 S | 10/2014 | Khalaj |
| 8,992,458 B2 | 3/2015 | Singh et al. |
| 8,998,854 B2 | 4/2015 | McKay |
| D737,435 S | 8/2015 | Ha et al. |
| D751,702 S | 3/2016 | Eaton et al. |
| D782,037 S | 3/2017 | Osypka |
| 9,764,122 B2 | 9/2017 | Clay et al. |
| 9,775,978 B2 | 10/2017 | Clay et al. |
| D802,755 S | 11/2017 | Snyder |
| D802,756 S | 11/2017 | Snyder |
| D802,757 S | 11/2017 | Snyder et al. |
| D809,652 S | 2/2018 | Snyder et al. |
| 10,076,650 B2 | 9/2018 | Koch et al. |
| 10,080,877 B2 | 9/2018 | Clay et al. |
| 10,384,048 B2 | 8/2019 | Clay et al. |
| 2001/0005785 A1 | 6/2001 | Sachse |
| 2001/0020147 A1 | 9/2001 | Staniforth et al. |
| 2001/0031940 A1 | 10/2001 | Loos |
| 2001/0033867 A1 | 10/2001 | Ahern et al. |
| 2001/0043915 A1 | 11/2001 | Frey |
| 2002/0009454 A1 | 1/2002 | Boone et al. |
| 2002/0022800 A1 | 2/2002 | O'Holloran et al. |
| 2002/0082583 A1 | 6/2002 | Lerner |
| 2002/0090398 A1 | 7/2002 | Dunn et al. |
| 2002/0116022 A1 | 8/2002 | Lebouitz et al. |
| 2002/0198527 A1 | 12/2002 | Muckter |
| 2003/0004491 A1 | 1/2003 | Tenhuisen et al. |
| 2003/0009235 A1 | 1/2003 | Manrique et al. |
| 2003/0023310 A1 | 1/2003 | Lubock et al. |
| 2003/0036673 A1 | 2/2003 | Schmidt |
| 2003/0039613 A1 | 2/2003 | Unger et al. |
| 2003/0045808 A1 | 3/2003 | Kaula et al. |
| 2003/0144570 A1 | 7/2003 | Hunter et al. |
| 2003/0171637 A1 | 9/2003 | Terwilliger et al. |
| 2003/0171954 A1 | 9/2003 | Guerin et al. |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0015133 A1 | 1/2004 | Karim |
| 2004/0015149 A1 | 1/2004 | Palasis |
| 2004/0034357 A1 | 2/2004 | Beane et al. |
| 2004/0054338 A1 | 3/2004 | Bybordi et al. |
| 2004/0064088 A1 | 4/2004 | Gorman et al. |
| 2004/0064193 A1 | 4/2004 | Evans et al. |
| 2004/0065615 A1 | 4/2004 | Hooper et al. |
| 2004/0072799 A1 | 4/2004 | Li et al. |
| 2004/0082540 A1 | 4/2004 | Hermida Ochoa |
| 2004/0082908 A1 | 4/2004 | Whitehurst et al. |
| 2004/0098113 A1 | 5/2004 | Forsell et al. |
| 2004/0106914 A1 | 6/2004 | Coppeta et al. |
| 2004/0109893 A1 | 6/2004 | Chen et al. |
| 2004/0111118 A1 | 6/2004 | Hill et al. |
| 2004/0162574 A1 | 8/2004 | Viola |
| 2004/0214793 A1 | 10/2004 | Hermida Ochoa |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2004/0228901 A1 | 11/2004 | Trieu et al. |
| 2004/0229878 A1 | 11/2004 | DiMauro et al. |
| 2004/0249464 A1 | 12/2004 | Bindseil et al. |
| 2005/0025765 A1 | 2/2005 | DiMauro et al. |
| 2005/0043673 A1 | 2/2005 | Lieberman |
| 2005/0070843 A1 | 3/2005 | Gonzales |
| 2005/0074481 A1 | 4/2005 | Brekke et al. |
| 2005/0079202 A1 | 4/2005 | Chen et al. |
| 2005/0107756 A1 | 5/2005 | McCraw |
| 2005/0137579 A1 | 6/2005 | Heruth et al. |
| 2005/0142163 A1 | 6/2005 | Hunter et al. |
| 2005/0143689 A1 | 6/2005 | Ramsey, III |
| 2005/0152905 A1 | 7/2005 | Omoigui |
| 2005/0152949 A1 | 7/2005 | Hotchkiss et al. |
| 2005/0175709 A1 | 8/2005 | Baty, III et al. |
| 2005/0177118 A1 | 8/2005 | Hoganson et al. |
| 2005/0177135 A1 | 8/2005 | Hildebrand et al. |
| 2005/0178779 A1 | 8/2005 | Wood |
| 2005/0184264 A1 | 8/2005 | Tesluk et al. |
| 2005/0186261 A1 | 8/2005 | Avelar et al. |
| 2005/0197293 A1 | 9/2005 | Mellis et al. |
| 2005/0203542 A1 | 9/2005 | Weber et al. |
| 2005/0245906 A1 | 11/2005 | Makower et al. |
| 2005/0249775 A1 | 11/2005 | Falotico et al. |
| 2005/0228620 A1 | 12/2005 | Shippert |
| 2005/0278023 A1 | 12/2005 | Zwirkoski |
| 2005/0287218 A1 | 12/2005 | Chaouk et al. |
| 2005/0288789 A1 | 12/2005 | Chaouk et al. |
| 2006/0046960 A1 | 3/2006 | McKay et al. |
| 2006/0046961 A1 | 3/2006 | McKay et al. |
| 2006/0074422 A1 | 4/2006 | Story et al. |
| 2006/0084943 A1 | 4/2006 | Roseman et al. |
| 2006/0100622 A1 | 5/2006 | Jackson |
| 2006/0106361 A1 | 5/2006 | Muni et al. |
| 2006/0121032 A1 | 6/2006 | Dahiyat et al. |
| 2006/0148903 A1 | 7/2006 | Burch et al. |
| 2006/0153815 A1 | 7/2006 | Seyda et al. |
| 2006/0161114 A1 | 7/2006 | Perot et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2006/0253100 A1 | 11/2006 | Burright et al. |
| 2006/0264839 A1 | 11/2006 | Veasey et al. |
| 2007/0005005 A1* | 1/2007 | Wang ............... A61M 37/0069 604/60 |
| 2007/0021358 A1 | 1/2007 | Edelman et al. |
| 2007/0043359 A1 | 2/2007 | Altarac et al. |
| 2007/0055378 A1 | 3/2007 | Ankney et al. |
| 2007/0066864 A1 | 3/2007 | Forde |

(56) References Cited

U.S. PATENT DOCUMENTS

| | | |
|---|---|---|
| 2007/0104769 A1 | 5/2007 | Feng et al. |
| 2007/0106247 A1 | 5/2007 | Burnett et al. |
| 2007/0118142 A1 | 5/2007 | Krueger et al. |
| 2007/0123863 A1 | 5/2007 | Winslow et al. |
| 2007/0129744 A1 | 6/2007 | Teichert et al. |
| 2007/0149992 A1 | 6/2007 | Teng |
| 2007/0156180 A1 | 7/2007 | Jaax et al. |
| 2007/0179474 A1 | 8/2007 | Cahill et al. |
| 2007/0185497 A1 | 8/2007 | Cauthen et al. |
| 2007/0202074 A1 | 8/2007 | Shalaby |
| 2007/0219564 A1 | 9/2007 | Rue et al. |
| 2007/0233038 A1 | 10/2007 | Pruit et al. |
| 2007/0243225 A1 | 10/2007 | McKay |
| 2007/0243228 A1 | 10/2007 | McKay |
| 2007/0244442 A1 | 10/2007 | Chowhan |
| 2007/0248639 A1 | 10/2007 | Demopulos et al. |
| 2007/0249632 A1 | 10/2007 | Zentner |
| 2007/0253994 A1 | 11/2007 | Hildebrand |
| 2007/0255281 A1 | 11/2007 | Simonton et al. |
| 2007/0255282 A1 | 11/2007 | Simonton et al. |
| 2007/0260184 A1 | 11/2007 | Justis et al. |
| 2007/0260201 A1 | 11/2007 | Prausnitz et al. |
| 2007/0265582 A1 | 11/2007 | Kaplan et al. |
| 2008/0004570 A1 | 1/2008 | Simonton et al. |
| 2008/0004703 A1 | 1/2008 | Trieu et al. |
| 2008/0009830 A1 | 1/2008 | Fujimoto et al. |
| 2008/0021074 A1 | 1/2008 | Cartt |
| 2008/0038351 A1 | 2/2008 | Beals et al. |
| 2008/0065029 A1 | 3/2008 | Racz |
| 2008/0077093 A1 | 3/2008 | Gratwohl et al. |
| 2008/0091207 A1 | 4/2008 | Truckai et al. |
| 2008/0102097 A1 | 5/2008 | Zanella |
| 2008/0125637 A1 | 5/2008 | Geist et al. |
| 2008/0139877 A1 | 6/2008 | Chu et al. |
| 2008/0208138 A1 | 8/2008 | Lim et al. |
| 2008/0215001 A1 | 9/2008 | Cowe |
| 2008/0228193 A1 | 9/2008 | Matityahu |
| 2008/0294039 A1 | 11/2008 | Jones et al. |
| 2009/0053211 A9 | 2/2009 | Lazar et al. |
| 2009/0088809 A1 | 4/2009 | Fisher et al. |
| 2009/0099597 A1 | 4/2009 | Isse |
| 2009/0131908 A1* | 5/2009 | McKay ............ A61B 17/3468 604/511 |
| 2009/0148500 A1 | 6/2009 | Lawter et al. |
| 2009/0177141 A1 | 7/2009 | Kucklick |
| 2009/0182267 A1* | 7/2009 | Painchaud ........ A61M 37/0069 604/60 |
| 2009/0246123 A1 | 10/2009 | Zanella et al. |
| 2009/0263319 A1 | 10/2009 | Wohabrebbi et al. |
| 2009/0263321 A1 | 10/2009 | McDonald et al. |
| 2009/0263441 A1 | 10/2009 | McKay |
| 2009/0263459 A1 | 10/2009 | King et al. |
| 2009/0263460 A1 | 10/2009 | McDonald |
| 2009/0264490 A1 | 10/2009 | Zanella et al. |
| 2009/0264491 A1 | 10/2009 | McKay et al. |
| 2010/0015049 A1 | 1/2010 | Wohabrebbi |
| 2010/0106132 A1 | 4/2010 | Simonton |
| 2010/0106136 A1 | 4/2010 | Simonton |
| 2010/0106137 A1 | 4/2010 | Simonton et al. |
| 2010/0160375 A1 | 6/2010 | King |
| 2010/0163059 A1 | 7/2010 | Tierney et al. |
| 2010/0198140 A1 | 8/2010 | Lawson |
| 2010/0249750 A1 | 9/2010 | Racz |
| 2010/0331874 A1 | 12/2010 | Bardy |
| 2011/0098675 A1* | 4/2011 | Schmalz ............ A61M 37/0069 604/506 |
| 2011/0104233 A1 | 5/2011 | Drapeau |
| 2011/0106110 A1 | 5/2011 | McKay |
| 2011/0152755 A1* | 6/2011 | Schmalz ............ A61B 17/3468 604/60 |
| 2011/0182849 A1 | 7/2011 | Haddock et al. |
| 2011/0202011 A1 | 8/2011 | Wozencrift |
| 2011/0313393 A1 | 12/2011 | Zanella |
| 2012/0022568 A1 | 1/2012 | Koblish et al. |
| 2012/0142648 A1 | 6/2012 | Biggs et al. |
| 2012/0142747 A1 | 6/2012 | Wilsey et al. |
| 2013/0116556 A1 | 5/2013 | Racz |
| 2013/0178822 A1* | 7/2013 | Hickingbotham ............ A61B 17/3468 604/506 |
| 2013/0261596 A1 | 10/2013 | McKay |
| 2014/0277459 A1 | 9/2014 | McCarthy |
| 2016/0022973 A1 | 1/2016 | Clay et al. |
| 2017/0143950 A1 | 5/2017 | Koch et al. |
| 2017/0354811 A1 | 12/2017 | Clay et al. |
| 2018/0001072 A1 | 1/2018 | Clay et al. |
| 2018/0126090 A1 | 5/2018 | Snyder |
| 2019/0015653 A1 | 1/2019 | Koch et al. |

FOREIGN PATENT DOCUMENTS

| | | |
|---|---|---|
| EP | 1 216 721 | 6/2002 |
| EP | 1 518 549 | 2/2007 |
| EP | 1 625 870 | 5/2008 |
| EP | 2 008 596 | 12/2008 |
| FR | 1 270 590 | 9/1961 |
| FR | 2 007 684 | 1/1970 |
| FR | 2 231 355 | 12/1974 |
| GB | 1379358 | 1/1975 |
| KR | 10-2006-0120103 | 11/2006 |
| WO | WO 93/20859 | 10/1993 |
| WO | WO 94/01166 | 1/1994 |
| WO | WO 1999/052573 | 10/1999 |
| WO | WO 2000/038574 | 7/2000 |
| WO | WO 2001/062272 | 8/2001 |
| WO | WO 2002/034116 | 5/2002 |
| WO | WO 2003/005961 | 1/2003 |
| WO | WO 2004/009776 | 1/2004 |
| WO | WO 2004/050688 | 6/2004 |
| WO | WO 2004/084819 | 10/2004 |
| WO | WO 2005/018468 | 3/2005 |
| WO | WO 2005/034998 | 4/2005 |
| WO | WO 2007/121288 | 10/2007 |
| WO | WO 2008/067362 | 6/2008 |
| WO | WO 2008/091777 | 7/2008 |
| WO | WO 2009/049823 | 4/2009 |
| WO | WO 2010/011526 | 1/2010 |
| WO | WO 2016/014300 | 1/2016 |

OTHER PUBLICATIONS

U.S. Appl. No. 08/386,853, filed Feb. 10, 1995, Method and Device for Administering Analgesics.

U.S. Appl. No. 08/775,528 (U.S. Pat. No. 5,980,927), filed Jan. 2, 1997 (Nov. 9, 1999), Method and Apparatus for Administering Analgesics, and Method for Making Same.

U.S. Appl. No. 09/291,571 (U.S. Pat. No. 6,214,370), filed Apr. 9, 1999 (Apr. 10, 2001), Method and Device for Administering Analgesics.

U.S. Appl. No. 10/932,878, filed Sep. 2, 2004, Controlled and Directed Local Delivery of Anti-Inflammatory Compositions.

U.S. Appl. No. 11/091,348, filed Mar. 28, 2005, Controlled and Directed Local Delivery of Anti-Inflammatory Compositions.

U.S. Appl. No. 11/932,442 (U.S. Pat. No. 8,029,478), filed Oct. 31, 2007 (Oct. 4, 2011), Implantable Device and Method for Delivering Drug Depots to a Site Beneath the Skin.

U.S. Appl. No. 13/220,086, filed Aug. 29, 2011, Implantable Device and Method for Delivering Drug Depots to a Site Beneath the Skin.

U.S. Appl. No. 11/942,820 (U.S. Pat. No. 8,221,358), filed Nov. 20, 2007 (Jul. 17, 2012), Devices and Methods for Delivering Drug Depots to a Site Beneath the Skin.

U.S. Appl. No. 12/260,673, filed Oct. 29, 2008, Drug Delivery Device with Sliding Cartridge.

U.S. Appl. No. 12/260,683, filed Oct. 29, 2008, Drug Delivery System.

U.S. Appl. No. 12/260,700, filed Oct. 29, 2008, Drug Cartridge for Deliverying a Drug Depot Comprising Superior and Inferior Covers.

U.S. Appl. No. 12/262,823 (U.S. Pat. No. 8,702,677), filed Oct. 31, 2008 (Apr. 22, 2014), Device and Method for Directional Delivery of a Drug Depot.

(56) References Cited

OTHER PUBLICATIONS

U.S. Appl. No. 12/507,197 (U.S. Pat. No. 8,715,223), filed Jul. 22, 2009 (May 6, 2014), Device and Method for Delivery of a Drug Depot Near the Nerve.

U.S. Appl. No. 12/609,934, filed Oct. 30, 2009, Devices and Methods for Implanting a Plurality of Drug Depots Having One or More Anchoring Members.

U.S. Appl. No. 12/693,853 (U.S. Pat. No. 8,267,895), filed Jan. 26, 2010 (Sep. 18, 2012), Needle Guide System.

U.S. Appl. No. 12/694,329 (U.S. Pat. No. 7,955,301), filed Jan. 27, 2010 (Jun. 7, 2011), Injection Shut Off Valve With Pressure Actuator for Delivery of Compositions.

U.S. Appl. No. 12/695,899 (U.S. Pat. No. 8,998,854), filed Jan. 28, 2010 (Apr. 7, 2015), Catheter Devices and Drainage Systems for Delivering Therapeautic Agents.

U.S. Appl. No. 11/403,733 (U.S. Pat. No. 7,741,273), filed Apr. 13, 2006 (Jun. 22, 2010), Drug Depot Implant Designs.

U.S. Appl. No. 12/715,093 (U.S. Pat. No. 8,418,064), filed Mar. 1, 2010 (Jul. 9, 2013), Method for Delivering a Therapeautic Agent Comprising Injection of Microspheres.

U.S. Appl. No. 11/734,618 (U.S. Pat. No. 7,727,954), filed Apr. 12, 2007 (Jun. 1, 2010), Drug Depot Implant Designs.

U.S. Appl. No. 12/716,383 (U.S. Pat. No. 8,357,388), filed Mar. 3, 2010 (Jan. 22, 2013), Drug Depot Implant Designs and Methods of Implantation.

U.S. Appl. No. 12/861,857 (U.S. Pat. No. 8,246,571), filed Aug. 24, 2010 (Mar. 1, 2012), Drug Storage and Delivery Device Having a Retaining Member.

U.S. Appl. No. 13/309,725, filed Dec. 2, 2011, Methods for Delivering Clonidine Compositions in Biodegradable Polymer Carrier and Local Steroids to a Target Tissue Site.

U.S. Appl. No. 13/309,759, filed Dec. 2, 2011, Compositions and Methods for Delivering Clonidine to a Target Tissue Site.

U.S. Appl. No. 14/341,026 (U.S. Pat. No. 10,080,877), filed Jul. 25, 2014 (Sep. 25, 2018), Pellet Delivery Device.

U.S. Appl. No. 29/569,125 (U.S. Pat. No. D. 809,652), filed Jun. 23, 2016 (Feb. 6, 2018), Pellet Delivery Device.

U.S. Appl. No. 14/341,461 (U.S. Pat. No. 9,775,978), filed Jan. 28, 2016 (Oct. 3, 0217), Drug Delivery Device and Methods Having a Retaining Member.

U.S. Appl. No. 15/703,512, filed Sep. 13, 2017, Drug Delivery Device and Methods Having a Retaining Member.

U.S. Appl. No. 14/949,118, filed Nov. 23, 2015, Enhanced Stylet for Drug Depot Injector.

U.S. Appl. No. 14/341,256 (U.S. Pat. No. 9,764,122), filed Jul. 25, 2014 (Sep. 19, 2017), Drug Delivery Device and Methods Having an Occluding Member.

U.S. Appl. No. 15/689,810 (U.S. Pat. No. 10,384,048), filed Aug. 29, 2017 (Aug. 20, 2019), Drug Delivery Device and Methods Having an Occluding Member.

U.S. Appl. No. 16/544,064, filed Aug. 19, 2019, Drug Delivery Methods Having an Occluding Member.

U.S. Appl. No. 29/569,092 (U.S. Pat. No. D. 802,755), filed Jun. 23, 2016 (Nov. 14, 2017), Drug Pellet Cartridge.

U.S. Appl. No. 29/569,107 (U.S. Pat. No. D. 802,756), filed Jun. 23, 2016 (Nov. 14, 2017), Drug Pellet Cartridge.

U.S. Appl. No. 29/569,123 (U.S. Pat. No. D. 802,757), filed Jun. 23, 2016 (Nov. 14, 2017), Drug Pellet Cartridge.

U.S. Appl. No. 15/345,764, filed Nov. 8, 2016, Drug Pellet Delivery System and Method.

* cited by examiner

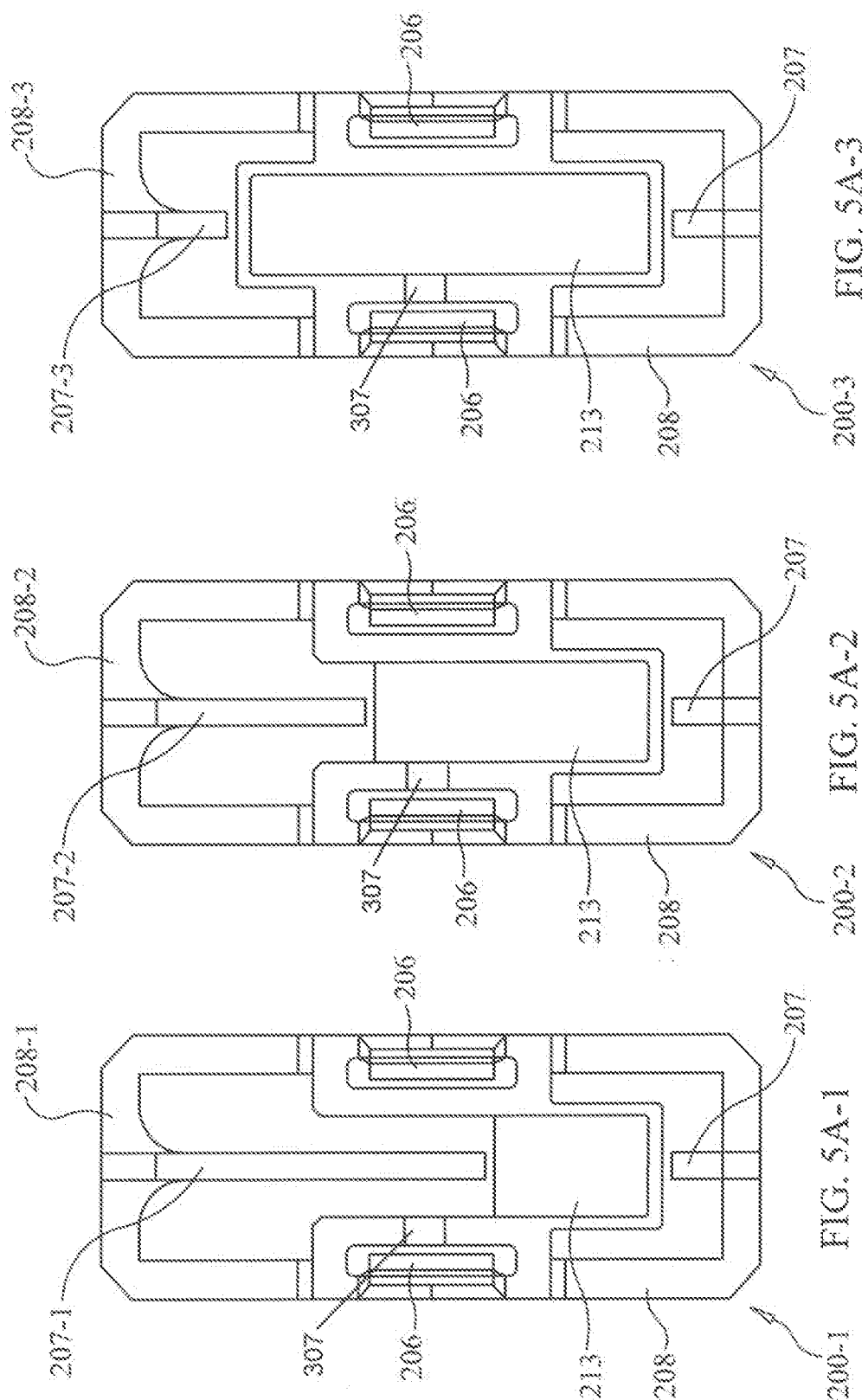

DRUG DELIVERY DEVICE AND METHODS HAVING A RETAINING MEMBER

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug depots have been developed, which allow a drug to be introduced or administered to sites beneath the skin of a patient. The drug depot releases the drug over a period of time. Drug depots allow the drug to be released from the depot in a relatively uniform dose over weeks, months or even years. Administering drugs using drug depots is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug depots are typically inserted into a treatment site beneath the skin of a patient by use of a trocar device, which is a two-piece device that includes a cannula and an obdurator. The trocar device requires an incision to be made through the skin using a separate instrument (e.g., scalpel) so that the drug depot can be moved through the incision to an implant site within the patient's anatomy. The cannula and obdurator may be inserted together through the incision. Next, the obdurator is withdrawn, leaving the cannula in place as a guide for inserting the drug depot. The drug depot is inserted through the cannula, and the obdurator is used to push the implant to the end of the cannula. The cannula and obdurator are then withdrawn completely, leaving the drug depot at the implant site.

Typically, trocar devices are used to implant drug depots subcutaneously over a large area (e.g., 2-2.5 inches), with a typical drug depot in the order of 1½ inches long. Thus, the trocar device is not suitable for many small or hard to reach treatment sites because it lacks precision and may cause additional trauma to the tissue surrounding the site of implant.

Other drug delivery devices have been developed that attempt to simplify implanting drug depots. These devices have a handle for one-handed implantation of a drug depot, a needle containing the drug depot to be implanted and a rod positioned within the needle for pushing the drug depot out of the needle. Once the needle containing the drug depot has been inserted at the site of implantation, a spring loaded trigger on the handle is activated, which causes the needle to be automatically withdrawn by a spring, thus leaving the drug depot at the site of implantation. Unfortunately, it is not possible to control the motion of the needle in these devices because the needle will automatically retract upon activation of the trigger. Furthermore, the complex spring loaded propelling system and trigger of these devices increase the likelihood that the device will jam and fail to eject the drug depot when required.

Conventional needle and syringe devices have also been used to implant a drug depot to sites within a patient, such as, for example, epidural space. These devices typically utilize a syringe that is preloaded with the drug depot. A needle of the syringe is inserted through the patient's skin, supraspinous ligament, intraspinous ligament, ligamentum flavum and into the epidural space. The drug depot is delivered through the needle to the epidural space by moving a plunger of the syringe relative to the needle. However, such devices do not allow for controlled and precision implantation of a drug depot. The ability to implant a drug depot in a controlled and precise manner is further reduced when such devices are used to implant multiple drug depots.

In devices used for drug depot implantation, drug depots are secured in a drug cartridge of the devices by use of a bulking agent. The bulking agent may be added to the drug depot to ensure the drug depot is secure within the drug cartridge, such that the drug depot is released when a plunger is engaged to dislodge the drug depot from the drug cartridge. The bulking agent may be added to the drug cartridge before the drug depot is added to the drug cartridge. The drug depot may also be added to the drug cartridge before the bulking agent is positioned within the drug cartridge, and the bulking agent is added to the drug cartridge after the drug depot has been positioned therein. Use of a bulking agent to retain the drug depot in a drug cartridge requires additional steps and is time consuming.

Treatment of patients with drug depots involves injecting one or a plurality of drug depots into the patient. In order to avoid injecting an incorrect number of drug depots, a drug delivery device should allow for visual verification of a number of drug depots loaded in the drug delivery device. Furthermore, since varying numbers of drug depots are used, it is desirable that a drug delivery device accommodate varying numbers of the drug depots. It is further desirable that a drug delivery device be tailored to specific numbers of drug depots. Still further, reliability of such drug delivery devices is important and such devices should therefore provide for jam free operation.

New drug delivery devices are needed, which can easily allow accurate and precise implantation of at least one drug depot with minimal physical and psychological trauma to a patient. When implanting a plurality of drug depots, a drug delivery device is needed that accurately and precisely allows placement of the drug depots in a manner such that one of the drug depot does not substantially interfere with the other drug depots.

SUMMARY

New drug delivery devices are provided that can easily allow accurate and precise implantation of at least one drug depot with minimal physical and psychological trauma to a patient.

Disclosed are drug delivery devices, kits that include at least one of the drug delivery devices and/or components of at least one of the drug delivery devices and methods for assembling the drug delivery devices and/or implanting at least one drug depot using the drug delivery devices.

In some embodiments, the drug delivery device comprises a housing and at least one drug cartridge, which optionally includes at least one occluding device to prevent unintended exit of a drug depot from the drug cartridge(s). The drug cartridges are configured for a differing number of drug depots. The housing includes a viewing aperture for verifying the number of drug depots within each of the drug cartridges. A plunger has a push rod for moving the drug depots through the drug delivery device for delivery to a site within the patient. The kit comprises at least the above components. The method includes assembling the components of the drug delivery device and delivering a selected number of drug depots into a patient using the drug delivery device.

In some embodiments, each of the drug cartridges defines a cartridge depot channel dimensioned to slidably accept at least one of the drug depots. At least one of the drug cartridges has at least a first occluding device configured to at least partially occlude the cartridge depot channel at a first occluding position to prevent the drug depots from moving past the first occluding position. A force is applied to at least one of the drug depots to deflect the first occluding device and permit at least one of the drug depots to move past the first occluding device. The housing has a coupling mechanism at a distal housing end for engaging the cannula. The push rod is slidably receivable in the cartridge depot channel to move at least one of the drug depots past the first occluding device, through the cannula and into the patient.

In some embodiments, the housing defines an aperture for viewing at least one of the drug cartridges, and at least one of the drug cartridges has a retaining panel arranged to retain at least one drug depot in the cartridge depot channel. In some embodiments, the retaining panel is transparent or translucent to permit visual verification of the presence of at least one of the drug depots in the drug cartridge via the aperture in the housing.

In some embodiments, at least one of the drug cartridges has an alignment boss at a distal cartridge end through which the cartridge depot channel passes. The alignment boss includes an opening at a distal end thereof that is in communication with the cartridge depot channel. The housing defines a cartridge cavity configured to accept one of the drug cartridges. The cartridge cavity has a proximal cavity end and a distal cavity end. The distal cavity end is proximal to the coupling mechanism. The opening in the alignment boss is in communication with the cartridge depot channel such that at least one of the drug depots can move through the cartridge depot channel and exit the cartridge depot channel through the opening that extends through the cartridge boss. In some embodiments, the opening in the alignment boss is coaxial with the cartridge depot channel such that at least one of the drug depots can move along a longitudinal axis through the cartridge depot channel, exit the cartridge depot channel through the opening that extends through the alignment boss and enter the cannula. The cartridge comprises a cartridge body that is positioned in a first portion of a cartridge cavity of the housing and the alignment boss is positioned in a second portion of the cartridge cavity, such as, for example, a receiving socket. The second portion has a diameter that is less than that of the first portion. In some embodiments, an inner surface of the housing that defines the second portion of the cartridge cavity engages an outer surface of the alignment boss to secure the alignment boss in the second portion of the cartridge cavity, such as, for example, a press fit manner that aligns the cartridge depot channel, the opening in the alignment boss and the cannula.

In some embodiments, at least one of the drug cartridges optionally includes a second occluding device configured to at least partially occlude the cartridge depot channel at a second occluding position. The second occluding device is spaced apart from the first occluding device a distance sufficient to accept at least one of the drug depots in the cartridge depot channel. The second occluding device is configured such that at least one of the drug depots cannot pass through the cartridge depot channel at the second occluding position without force being applied to at least one of the drug depots to deflect the second occluding device to move at least one of the drug depots past the second occluding device. In some embodiments, the second occluding device has a length sufficient to accept a maximum of one drug depot in the cartridge depot channel between the first and second occluding devices. In some embodiments, the second occluding device has a length sufficient to accept a maximum of two drug depots in the cartridge depot channel between the first and second occluding devices. In some embodiments, the second occluding device has a length sufficient to accept a maximum of three drug depots in the cartridge depot channel between the first and second occluding devices.

In some embodiments, the first and second occluding devices are respectively first and second cantilever arms each having a ramped protruding portion extending into and at least partially occluding the cartridge depot channel respectively at the first and second occluding positions. In some embodiments, the drug cartridge is positioned within the housing such that the drug cartridge cannot be removed from the housing without breaking the housing. In some embodiments, the device includes a locking feature configured to allow the drug cartridge to be inserted into the housing, but prevents the drug cartridge from being removed from the housing.

In some embodiments, the ramped protruding portions of the first and second occluding devices each include a ramp and a plateau. The push rod is configured to push at least one of the drug depots such that at least one of the drug depots slides along the ramp of the first occluding device and onto the plateau of the first occluding device. At least one of the drug depots slides along the plateau of the first occluding device and into the cartridge depot channel. The push rod is used to move at least one of the drug depots from the cartridge depot channel and onto the ramp of the second occluding device. At least one of the drug depots slides along the ramp of the second occluding device and onto the plateau of the second occluding device. At least one of the drug depots slides along the plateau of the second occluding device and into the cannula.

The housing includes a lower body and an upper body. The housing extends in a longitudinal direction between a housing upper end and a housing lower end. The lower body has a lower body bottom end, a lower body upper end, and an annular step surface extending inward from an outer periphery of the lower body. The lower body defines a lower body channel extending in the longitudinal direction. The lower body channel has an opening at the lower body upper end and an opening at the lower body bottom end. The lower body bottom end includes the coupling mechanism of the drug delivery device. The coupling mechanism is configured for engaging a proximal end of the cannula with the housing. The upper body has an upper body top end and an upper body bottom end. The upper body defines an upper body channel that is open to the upper body top end. The upper body is connected to the lower body. A ring member has a ring top end and a ring bottom end. In some embodiments, the ring member extends upward from the annular step surface toward the housing upper end such that the ring member contacts at least one of the upper body and the lower body. The plunger of the drug delivery device has the push rod slidably receivable in the upper body channel, the depot channel and the lower body channel. The push rod has a push rod end configured to contact at least one of the drug depots when at least one drug depot is disposed in the drug cartridge. Upon application of force, the push rod moves at least one of the drug depots through the drug delivery device and into the site beneath the skin of the patient.

In some embodiments, the ring member of the drug delivery device is selected from a plurality of ring members that each includes indicia. The indicia may correspond to one or more of the drug depots, such as, for example, a feature of one or more of the drug depots and/or the maximum number of drug depots the drug cartridge can hold. The selected ring member is slid onto the upper body or the lower body. In some embodiments, the indicia includes either or both of alphanumeric labeling or color coding to facilitate selection of a drug delivery device containing the correct drug.

In some embodiments, the drug cartridge comprises a first cartridge plate and a second cartridge plate that is removably attached to the first cartridge plate. The first cartridge plate and the second cartridge plate, in combination, define the cartridge depot channel. At least one of the first and second cartridge plates comprises a cartridge engagement structure that secures the first cartridge plate to the second cartridge plate. In some embodiments, the engagement structure is disposed between a distal cartridge end and an opposite proximate cartridge end of the drug cartridge. In some embodiments, the cartridge engagement structure comprises engaging members, such as, for example, first and second prongs. In some embodiments, the first and second prongs extend respectively from first and second opposing lateral sides of one of the first and second cartridge plates. The other one of the first and second cartridge plates comprises engaging openings configured to engage the first and second prongs. In some embodiments, the second cartridge plate comprises the first occluding device discussed above. In some embodiments, the first cartridge plate comprises the second occluding device discussed above.

The push rod has a length that is long enough to adequately expel the drug depot through the combined length of the housing and the cannula. In some embodiments, the push rod has a length that is less than the combined length of the housing and the cannula. That is, the push rod does not and cannot extend to or beyond the distal tip of the needle. In some embodiments, the push rod has a length that is greater than or equal to the combined length of the housing and the cannula such that the push rod can be inserted into the housing and through the cannula such that the push rod extends entirely through the cannula. In some embodiments, the push rod has a length that is greater than the combined length of the housing and the cannula such that the push rod can be inserted into the housing and through the cannula such that the push rod extends entirely through the cannula and out of an opening in a distal tip of the cannula. In some embodiments, the device and/or kit includes a plurality of push rods that have different lengths and/or a plurality of cannulas that have different lengths. For example, in some embodiments, the device and/or kit includes a first push rod and a first cannula each having a length configured to deliver a drug depot into a petite patient, where the cannula does not need to penetrate deep into the patient. In some embodiments, the device and/or kit includes a second push rod and a second cannula, wherein at least one of second push rod and second cannula have a length that is greater than that of the first push rod and/or the first cannula such that the second push rod and the second cannula are configured to deliver a drug depot into a normal patient, where the second cannula needs to penetrate deeper into the patient, than with a petite patient. In some embodiments, the device and/or kit includes a third push rod and a third cannula, wherein at least one of the third push rod and the third cannula have a length that is greater than that of the second push rod and/or the second cannula such that the third push rod and the third cannula are configured to deliver a drug depot into an obese patient, where the third cannula needs to penetrate deeper into the patient, than with a normal patient.

In some embodiments, the kit comprises one or a plurality of drug cartridges that are the same or similar to the drug cartridges discussed above. The drug cartridges each have at least the first occluding device. One of the drug cartridges may be configured to accept a first number of drug depots and another one of the drug cartridges may configured to accept a second number of drug depots that is different than the first number of drug depots.

In some embodiments, the method includes delivering at least one drug depot using at least one of the drug depot delivery devices discussed above. In some embodiments, the method comprises selecting one of the drug cartridges discussed above as a selected drug cartridge. In some embodiments, the drug cartridge selected is based upon the maximum number of drug depots the drug cartridge can hold. That is, if only one drug depot is going to be delivered into a patient, a drug cartridge that holds a maximum of one drug depot may be selected. Likewise, if two drug depots are going to be delivered into a patient, a drug cartridge that holds a maximum of two drug depots may be selected. Etc. The selected drug cartridge is loaded with a selected number of drug depots. The selected drug cartridge is installed in the housing of the drug delivery device. The cannula is coupled to the housing. The number of drug depots that are in the selected drug cartridge is visually verified by looking through the aperture in the selected drug cartridge. The cannula is inserted into the patient. One or a plurality of the drug depots are implanted into the patient by inserting the push rod of the drug delivery device into the cartridge depot channel and advancing the push rod to move at least one of the drug depots into the patient through the cannula. In some embodiments, the method includes inserting the cannula into the patient such that a distal tip of the cannula is positioned adjacent to a selected implant site within the patient's anatomy.

In some embodiments, at least one of the drug depots is pre-loaded into the drug delivery device. That is, the user does not need to load the drug depot(s) into the drug delivery device. Rather, the drug depot(s) is/are positioned within the drug delivery device upon receiving the device. In some embodiments, the drug delivery device is configured to be loaded with at least one drug depot during assembly of the drug delivery device. In some embodiments, the drug delivery device includes a drug cartridge that is configured to be breach loaded with drug depots after assembly of the drug delivery device.

Additional features and advantages of the present disclosure will be set forth in part in the description that follows, and in part will be apparent from the description, or may be learned by practice of the present disclosure. The objectives and other advantages of the present disclosure will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 5A-1 is a side elevation view of a first cartridge plate of the drug delivery device shown in FIG. 1A that is configured be installed on the funnel body of FIGS. 4A and 4B and to hold one drug depot;

FIG. 5A-2 is a side elevation view of a first cartridge plate of the drug delivery device shown in FIG. 1A that is configured to be installed on the funnel body of FIGS. 4A and 4B and to hold two drug depots;

FIG. 5A-3 is a side elevation view of a first cartridge plate of the drug delivery device shown in FIG. 1A that is configured to be installed on the funnel body of FIGS. 4A and 4B and to hold three drug depots;

FIG. 5B-1 is a perspective view of a first cartridge plate of the drug delivery device shown in FIG. 1A that is configured to be installed on the funnel body of FIGS. 4A and 4B and to hold one drug depot;

FIG. 5B-2 is a perspective view of a first cartridge plate of the drug delivery device shown in FIG. 1A that is configured to be installed on the funnel body of FIGS. 4A and 4B and to hold two drug depots;

FIG. 5B-3 is a perspective view of a first cartridge plate of the drug delivery device shown in FIG. 1A that is configured to be installed on the funnel body of FIGS. 4A and 4B and to hold three drug depots;

Figure 1A:
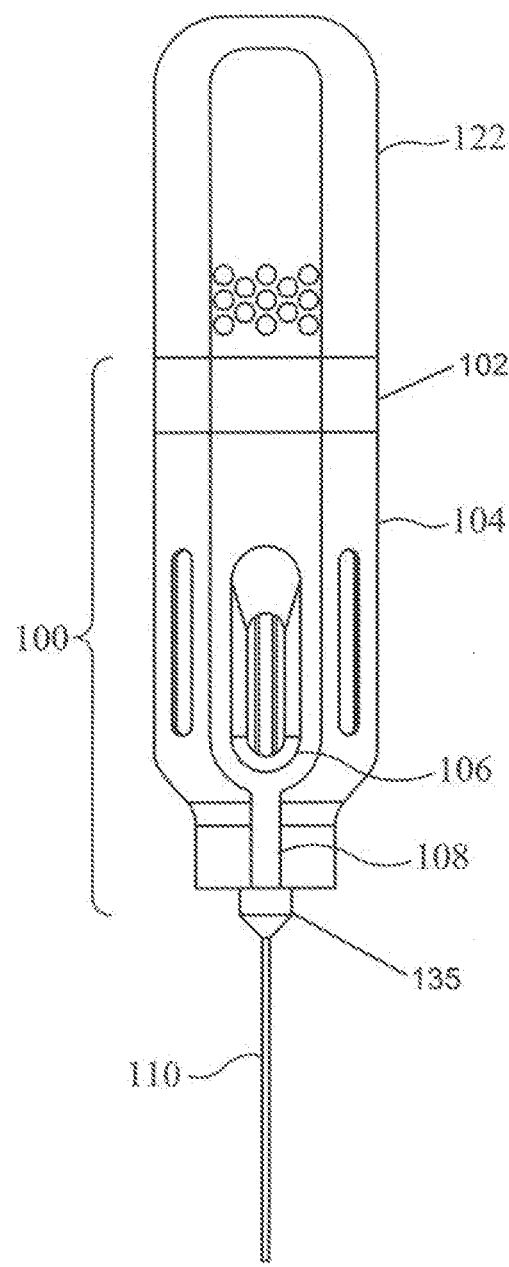
FIG. 1A is a front elevation view of a drug delivery device in accordance with the principles of the present disclosure.

It is to be understood that the figures are not drawn to scale but that elements of the figures shown are drawn to scale relative to one another. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

It is to be further understood that the doctrine of claim differentiation is to be applied between independent claims and their dependents and is not intended to be applied across independent claims. For example, the term A in a first independent claim may be interpreted to have the same scope as term B in a second independent claim, while if term A is in a first independent claim and term B further defines term A in claim dependent from the first independent claim, then term A must have a broader scope than term B. In other words, phrases that differ from one independent claim to another independent claim may be interpreted to have equal scope and read on common structure yet present the structure using different terminology in order to account for differing interpretation of phrase language.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the embodiments to those embodiments. On the contrary, the embodiments are intended to cover all alternatives, modifications, and equivalents, which may be included within the embodiments as defined by the appended claims.

The headings below are not meant to limit the disclosure in any way; embodiments under any one heading may be used in conjunction with embodiments under any other heading.

New drug delivery devices, which can easily allow the accurate and precise implantation of multiple drug depots with minimal physical and psychological trauma to a patient are provided. In some embodiments, the drug delivery device allows the user to dispense multiple drug depots, in sequence, to a site beneath the skin of the patient. In some embodiments, the drug delivery device allows the user to dispense multiple drug depots in sequence.

Definitions

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or within about 5 cm, for example) thereto. "Targeted delivery system" provides delivery of one or more drugs depots in a quantity of pharmaceutical composition that can be deposited at the target site as needed for treatment of pain, inflammation or other disease or condition.

Drug Delivery Device

Figure 1B:
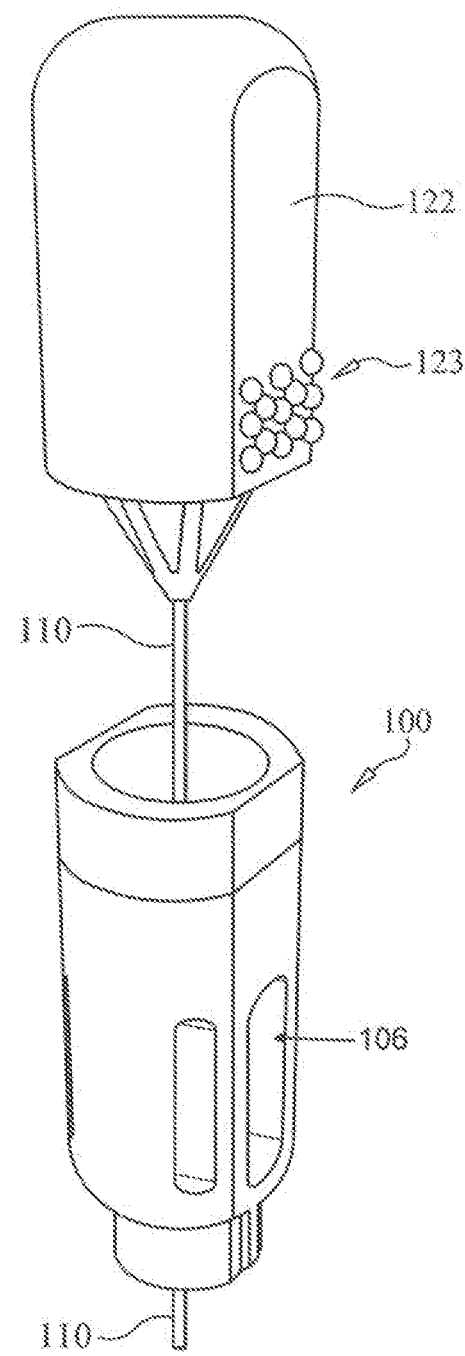
FIG. 1B is a perspective view of the drug delivery device shown in FIG. 1A, with part partially separated.
Figure 1C:
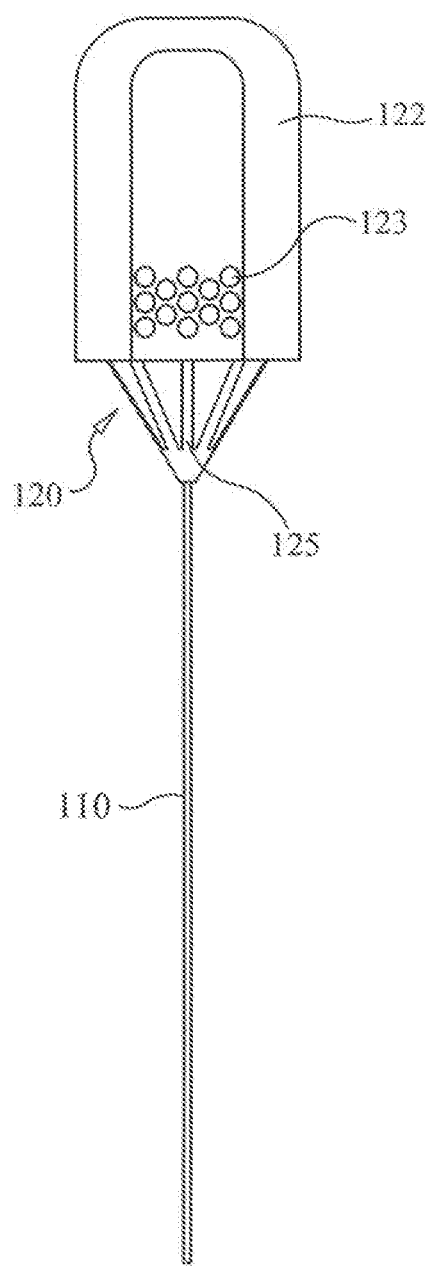
FIG. 1C is a front elevation view of a plunger of the drug delivery device shown in FIG. 1A.
Figure 3:
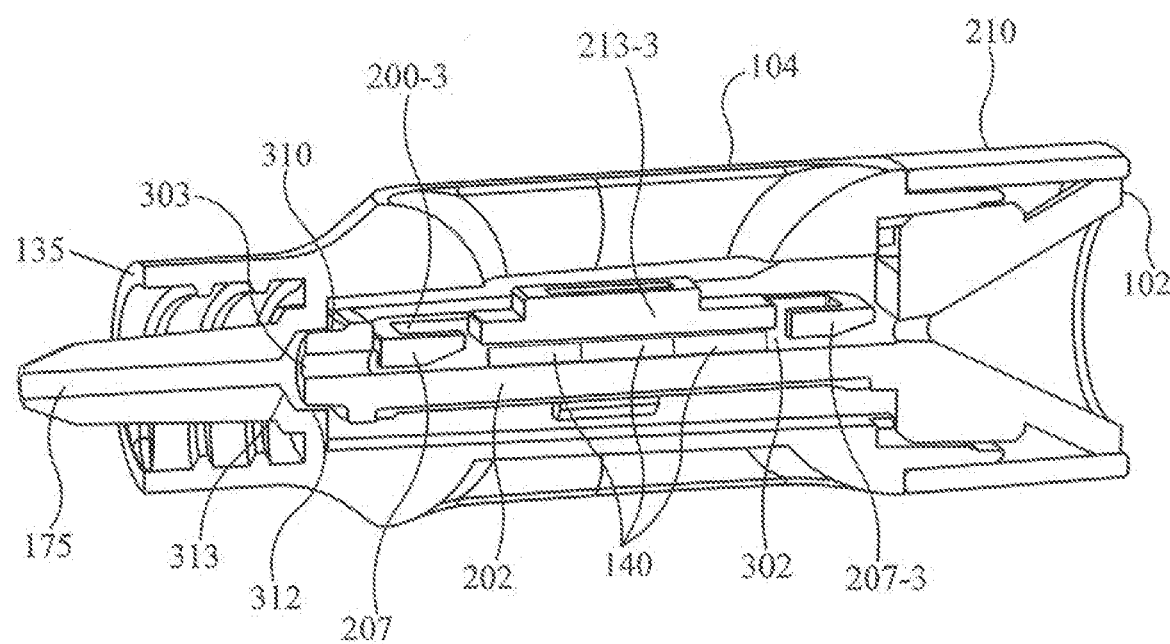
FIG. 3 is a cross-sectional view of a housing of the drug delivery device shown in FIG. 1A, with a drug cartridge configured for three drug depots installed, taken along line III-III of FIG. 2C.

Referring to FIGS. 1A-1C, the drug delivery device comprises a housing 100, a push rod 110, and a plunger 120 coupled to push rod 110. The plunger 120 has a knob 122 with an optional raised surface pattern 123. The raised surface pattern 123 provides for tactile grip of the knob 122. The illustrated raised surface pattern 123 is merely exemplary, and various modified patterns may be used. For example, the housing 100 comprises a main housing, such as, for example, a housing body 104 (FIGS. 1A and 1B) and a funnel body 102 (FIG. 3). In some embodiments, the housing body 104 defines a viewing aperture 106 (FIGS. 1A and 1B) configured to allow viewing of a drug cartridge (discussed below) and/or at least one drug depot within the housing body 104 so as to confirm presence of one or more drug depots within the drug cartridge and/or to verify that the proper type of drug depots are positioned within the drug cartridge. In some embodiments, the viewing aperture 106 is sized to permit viewing of multiple drug depots that are loaded into the drug cartridge. In some embodiments, the viewing aperture 106 is sized to permit viewing of only one drug depot that is loaded into the drug cartridge.

When push rod 110 is inserted through housing body 104, plunger knob 122 engages a proximal end of housing body 104, as shown in FIG. 1A. In some embodiments, an outer surface of plunger 120 engages an inner surface of housing body 104 when knob 122 engages the proximal end of housing body 104. In some embodiments, the outer surface of plunger knob 122 optionally has alignment ridges 125 which are configured to for disposal in corresponding grooves in the inner surface of housing body 104 to align plunger knob 122 with housing body 104. Additionally, it is envisioned that alignment ridges 125 provide structural support for the push rod 110. In some embodiments, housing body 104 is configured to be coupled to a cannula such that one or a plurality of drug depots will move through the cannula after the drug depots are expelled from housing body 104, as discussed herein. This allows a distal end of the cannula to be positioned adjacent to a target location at which the drug depots are to be implanted. The drug depots will exit the cannula through an opening in a distal end of the cannula after the drug depots are expelled from housing body 104 to deliver the drug depots to the target location. In some embodiments, the cannula is coupled to housing body 104 via a luer lock. An indicator ridge 108 is optionally provided on the housing body 104 such that when proper coupling of the luer lock is made, a corresponding ridge on a luer lock portion of the cannula aligns with the indicator ridge 108 of the housing body 104. Prior to disposing the drug depots in the patient, the user visually confirms presence of a correct number and type of the drug depots via the viewing aperture 106. In some embodiments, the cannula has a proximal end engaged to the housing 100 via a coupling device 135 (see, e.g., FIG. 1A). In some embodiments, the coupling device 135 comprises a luer lock, as discussed herein. In some embodiments, the coupling device 135 comprises threading fitting, friction fit fitting, or another fitting mechanism to functionally couple the cannula to the housing 100 so as to permit passage of at least one drug depot through the cannula and exit at a distal end of the cannula. In some embodiments, the cannula is hollow and has a sufficient diameter to allow passage of at least one of the drug depots. In some embodiments, the push rod 110 is configured to move at least one of the drug depots out of the drug cartridge. The distal end of the cannula is capable of insertion to a site beneath the skin. The size of the cannula is dictated by the procedure.

Figure 2A:
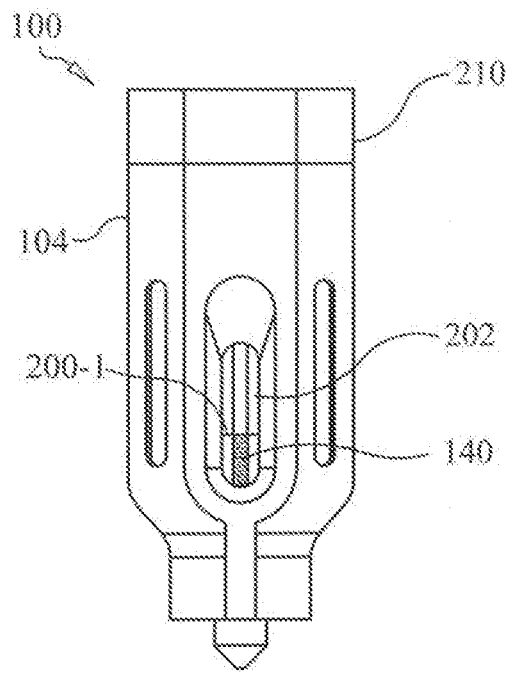
FIG. 2A is a front side elevation view of an assembled housing of a drug delivery device in accordance with the present disclosure that includes a drug cartridge configured for a maximum of one drug depot.
Figure 2B:
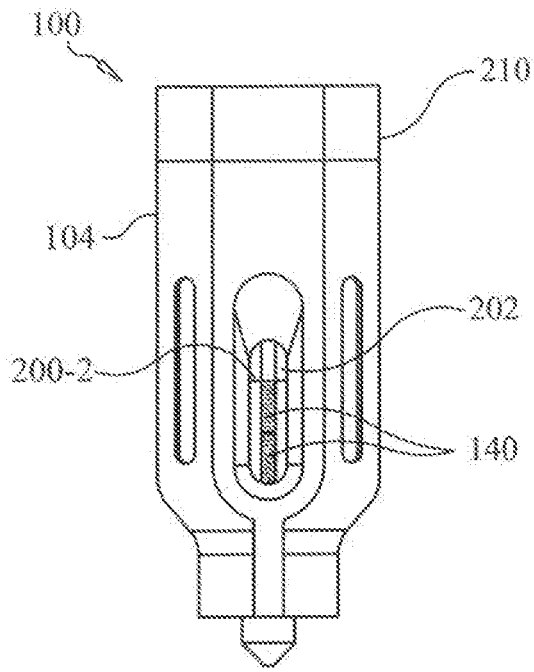
FIG. 2B is a front side elevation view of an assembled housing of the drug delivery device shown in FIG. 1A that includes a drug cartridge configured for a maximum of two drug depots.
Figure 2C:
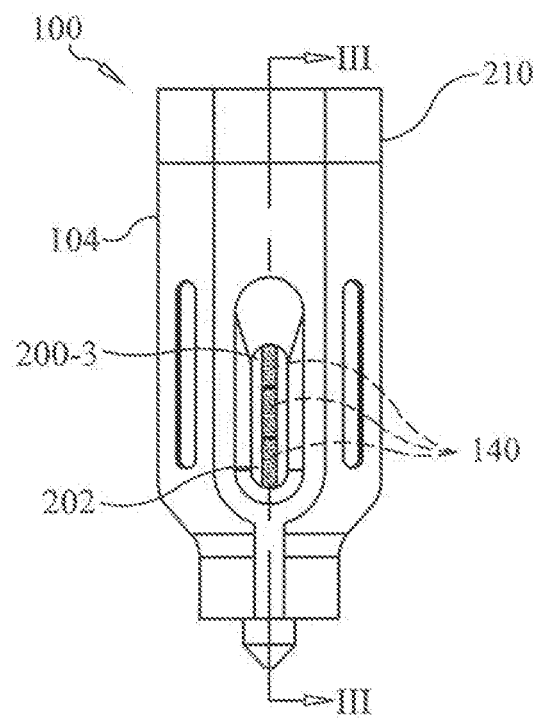
FIG. 2C is a front side elevation view of an assembled housing of the drug delivery device shown in FIG. 1A that includes a drug cartridge configured for a maximum of three drug depots.

In some embodiments, the drug depots each comprise a drug pellet, such as, for example, drug depots 140 (FIG. 2C). Drug depots 140 may include any drug or combination of drugs. For example, in one embodiment, at least one of drug depots 140 includes an effective amount of clonidine and a biodegradable polymer.

Figures 1, 5B:
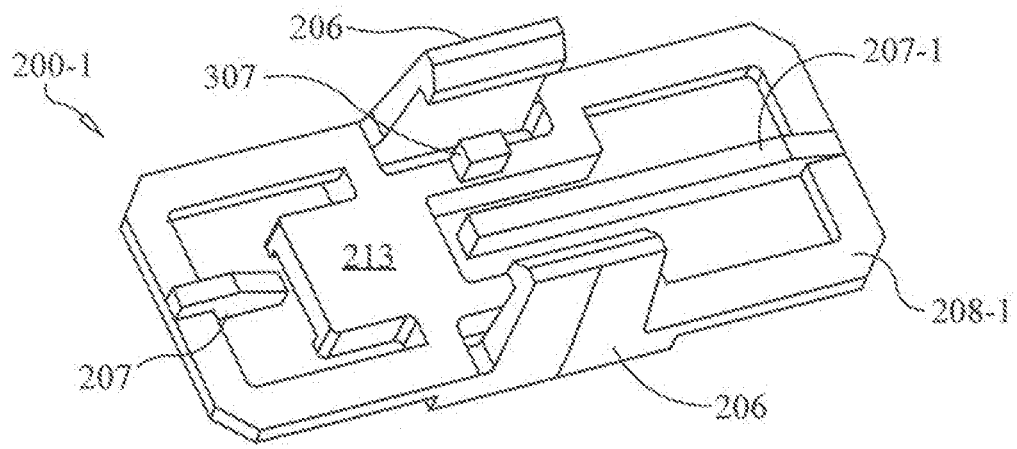
Figures 2, 5B:
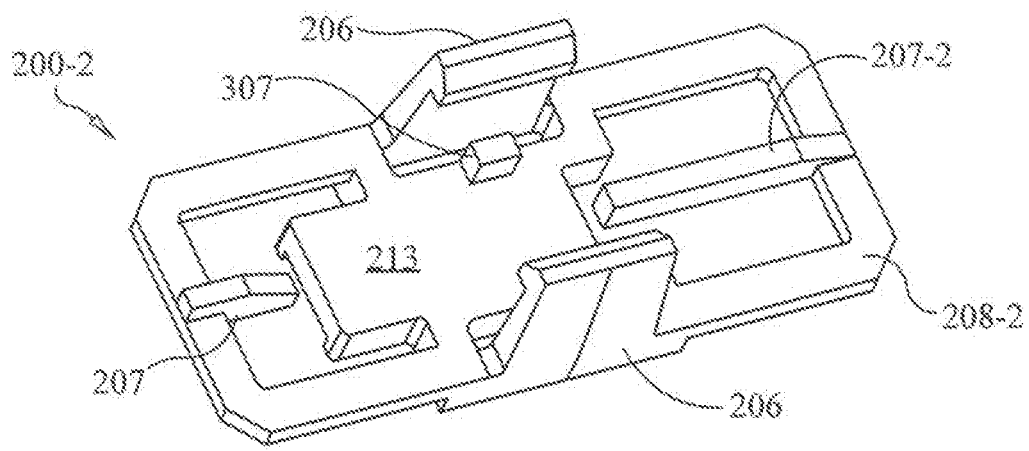
Figures 3, 5B:
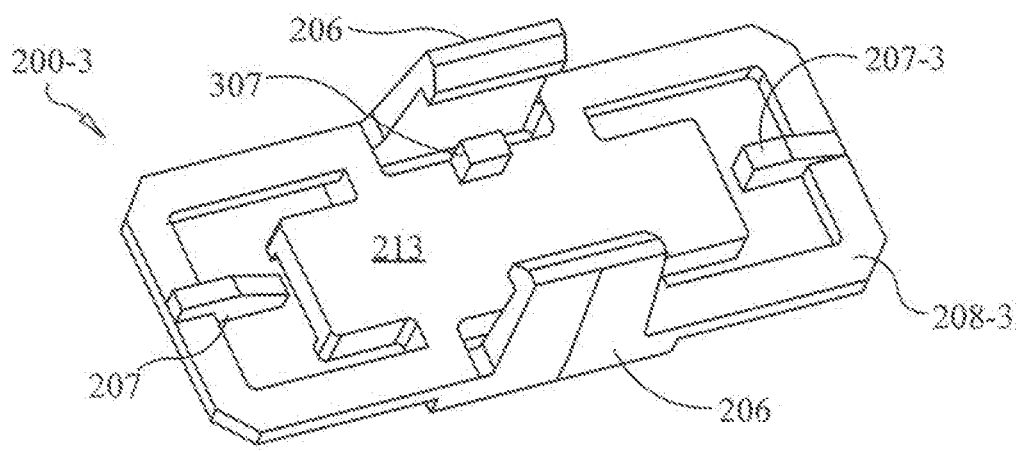

Referring to FIGS. 2A-2C, housing 100 comprises a main housing, such as, for example, housing body 104 and a first ring member 210. The drug delivery device includes a drug cartridge that is adaptable to selectively hold one or more drug depots, such as, for example, drug depots 140, by virtue of selection of one of the cartridge plates 200-1 to 200-3. FIGS. 2A and 5A-1 depict the cartridge plate 200-1, which is adapted to hold one drug depot, such as, for example, one drug depot 140. FIGS. 2B and 5A-2 depict cartridge plate 200-2, which is adapted to hold two drug depots, such as, for example, two drug depots 140. FIGS. 2C and 5A-3 depict cartridge plate 200-3, which is adapted to hold three drug depots, such as, for example, three drug depots 140. It is to be understood that the plates 200-1-200-3 may be adapted in accordance with the scope and spirit of this disclosure to hold varying number of drug depots, such as, for example, drug depots 140, and is not limited to a maximum of three drug depots or size increments of one drug depot.

Referring to FIG. 3, in some embodiments, the funnel body 102 has a cartridge plate 202 integrally formed therewith. In some embodiments, the cartridge plate 202 is formed separately from the funnel portion of the funnel body 102 and joined by a suitable engagement structure with complementary portions incorporated into the cartridge plate 202 and the funnel portion, as described below. In some embodiments, the housing body 104 may serve to secure together one of the cartridge plates 200-1-200-3 with cartridge plate 202.

Figure 4A:
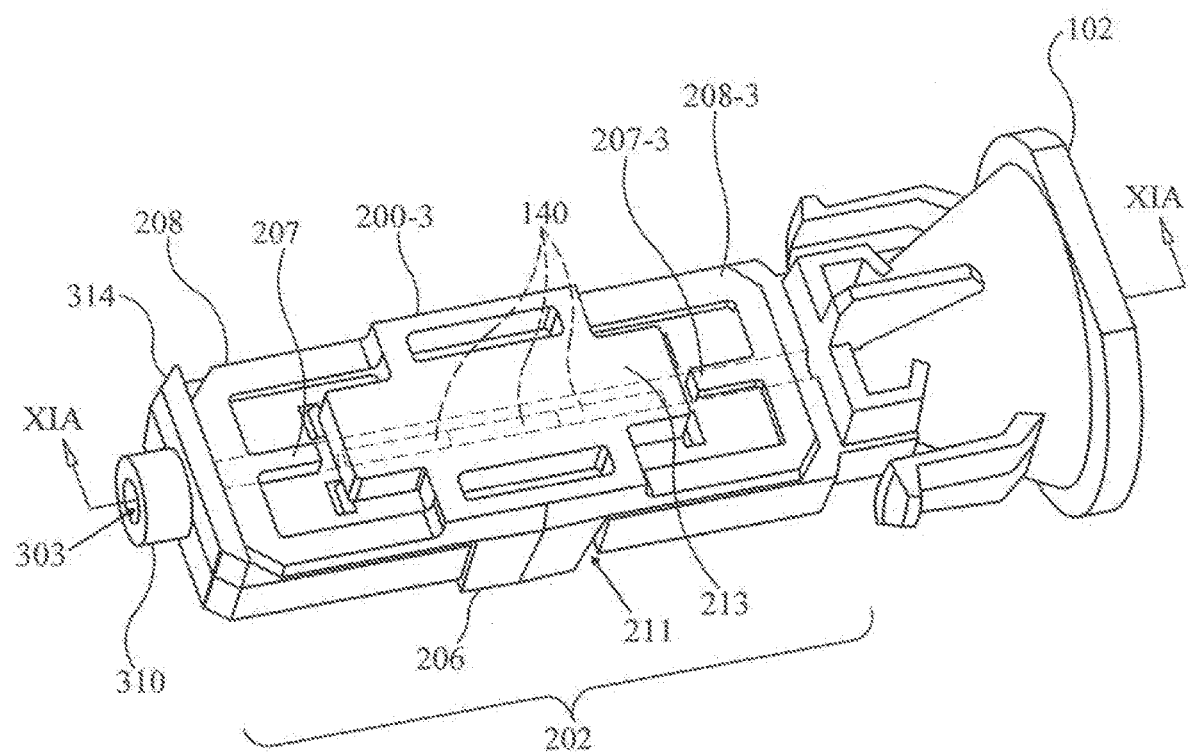
FIG. 4A is a perspective view of a funnel body having a second drug cartridge plate and a first cartridge plate, each of the drug delivery devices shown in FIG. 1A.
Figure 4B:
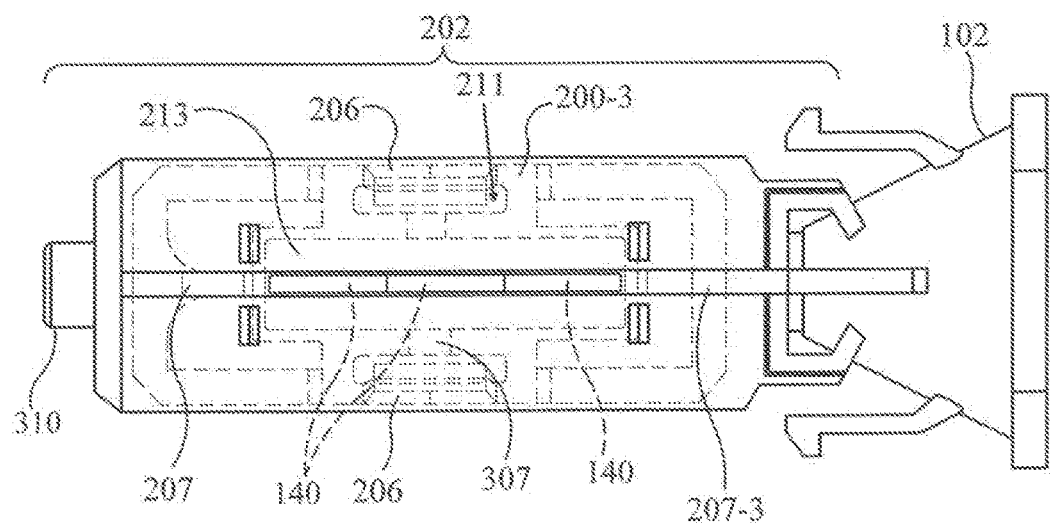
FIG. 4B is a front side elevation view of a funnel body, a first drug cartridge plate, and a second drug cartridge plate, each of the drug delivery devices shown in FIG. 1A.

The cartridge plate 202 engages one of the cartridge plates 200-1-200-3, as illustrated in FIGS. 3-4B. In some embodiments, cartridge plates 200-1-200-3, shown individually in FIGS. 5A-1 through 5B-3, are formed of a transparent or translucent material allowing the depot depots 140 to be viewed. In some embodiments, the cartridge plate 202 may also be formed of a translucent or transparent material to allow viewing of the depot depots 140 from an opposite end of the housing 100. In some embodiments, at least one of cartridge plates 200-1-200-3 include a mesh, slotted, or perforated material to allow viewing of the depot depots 140. As shown in FIGS. 2A-2C, cartridge plates 200-1-200-3 are configured to respectively hold one, two, or three drug depots, such as, for example, drug depots 140. In some embodiments, the cartridge plates 200-1-200-3 may be colored differently than the cartridge plate 202 such that, when viewed through the viewing aperture 106, the fifth cartridge plates 200-1-200-3 may be readily distinguished from the sixth cartridge plate 202.

The funnel body 102 is inserted into a housing body 104 with one of the cartridge plates 200-1-200-3 installed thereon. Cartridge plate 202 has a bottom wall 314 from which an alignment boss 310 protrudes, as shown in FIG. 4A. An end channel 303 extends through an end surface 311 of the alignment boss 310. The end channel 303 is in communication with a cartridge cavity of the housing 100 of the drug depot delivery device, as discussed herein. The alignment boss 310 engages a receiving socket 312 in a bottom portion of the housing body 104, as shown in FIG. 3 In some embodiments, the cartridge cavity of the housing 100 defines a first portion of the cartridge cavity and the receiving socket 312 defines a second portion of the cartridge cavity. The second portion has a diameter that is less than that of the first portion. The alignment boss 310 and the receiving socket 312 provide for precise alignment of a nipple channel 175 of the coupling device 135 of housing 100 with the end channel 303 of the alignment boss 310 (FIG. 3) to reduce incidences of a depot, such as, for example, one of drug depots 140, jamming when transferring the drug depot 140 between the drug cartridge and the nipple channel 175. In some embodiments, the alignment boss 310 and the receiving socket 312 are complementary tapered to provide for ease of insertion. Cartridge plate 202 has the end channel 303 formed as a conduit closed at the top. This further reduces the likelihood that a depot such as, for example, one of drug depots 140, will jam as it holds the drug depot 140 longitudinally aligned in place of a cantilever C-arm, which flexes as the drug depot 140 passes under it, as discussed herein.

The end channel 303 refers to a channel or conduit configured to accept a full diameter of a drug depot, such as, for example, one of drug depots 140. In some embodiments, the channels or conduits have a semicircular configuration. In some embodiments, alternative shapes may be employed which permit passage of the drug depots 140. In some embodiments, the shape of the channels or conduits does not conform to the shape of the drug depots 140.

Figure 6A:
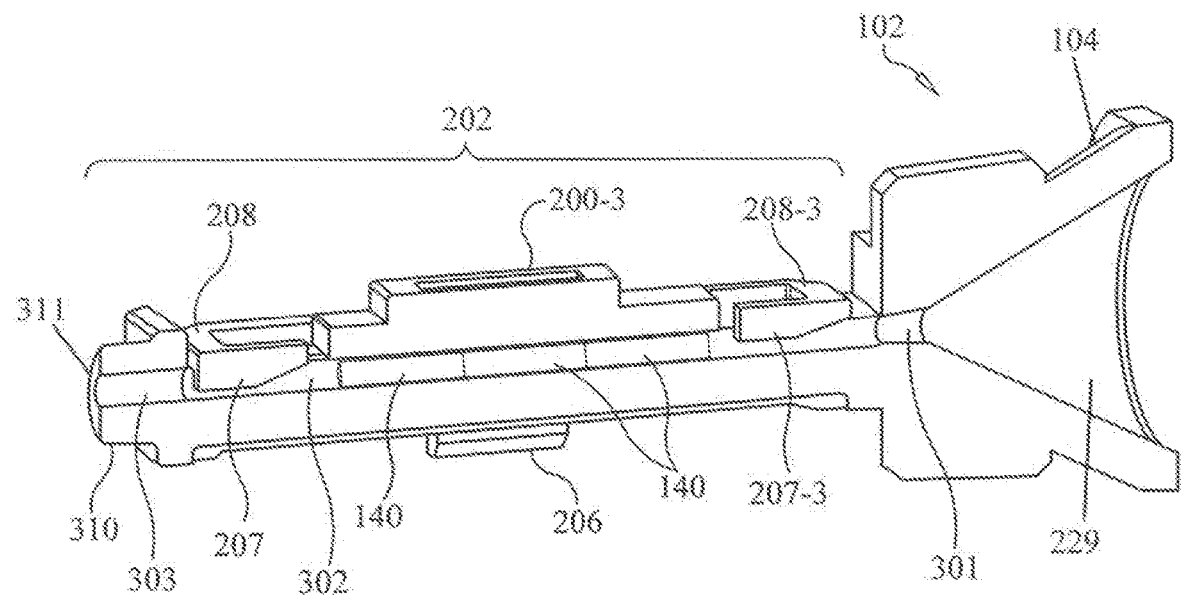
FIG. 6A is cross-sectional view of the funnel body of the drug delivery device shown in FIG. 4A taken along line XIA-XIA.

Cartridge plate 202 includes a main channel 302 that extends from a first end of cartridge plate 202 and communicates with the end channel 303 to an opposite second end of cartridge plate 202 that communicates with a tapered bore 301 of a funnel 229 of funnel body 102, as shown in FIG. 6A. Tapering of the tapered bore 301 permits ease of loading the depot depots 140. In some embodiments, the bore 301 is a straight bore, or a straight bore with a beveled intake. The end channel 303 is optionally dimensioned slightly larger than the main channel 302 to permit some play so that the drug depot 140 may be guided by a beveled socket bottom 313 (FIG. 3) into the nipple channel 175. The end channel 303 in combination with the main channel 302 form a cartridge depot channel.

Cartridge plates 200-1-200-3 each include a pellet retaining panel 213. Pellet retaining panel 213 is shown in FIG. 3 as pellet retaining panel 213-3 Pellet retaining panels 213 are respectively sized in their longitudinal direction to retain one, two, or three drug depots, such as, for example, drug depots 140 in the main channel 302 when one of cartridge plates 200-1-200-3 is snapped onto cartridge plate 202 with the depot depots 140 positioned in the main channel 302, as shown in FIGS. 2A-4B. In some embodiments, the pellet retaining panels 213 are flat on their rear sides to cover the main channel 302 and thereby retain the drug depots 140 therein. In some embodiments, the pellet retaining panels 213 have an indented channel for permitting passage of the drug depot 140 with an axis of a resulting conduit being aligned with axes of the end channel 303 and the tapered bore 301.

Cartridge plates 200-1-200-3 have catch hook arms 206 at positions along longitudinal sides of cartridge plates 200-1-200-3. Catch hook arms 206 fit in the notches 211 in cartridge plate 202 to engage the cartridge plate 202 with one of cartridge plates 200-1-200-3, as shown in FIGS. 4A and 4B. Adjacent to the catch hook arms 206 on right sides of cartridge plates 200-1-200-3 is a polarizing boss 307 that engages a corresponding indentation in cartridge plate 202 to prevent installation of cartridge plates 200-1-200-3 in an incorrect orientation.

Figure 6B:
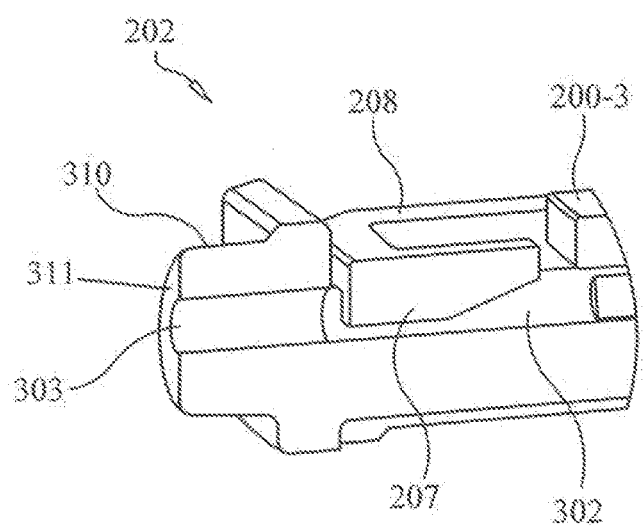
FIG. 6B is an enlarged cross-sectional view of a bottom portion of a funnel body and first cartridge plate of the drug delivery device shown in FIG. 6A.

Cartridge plates 200-1-200-3 each have a first occluding device, such as, for example, a cantilever C-arm 208 and a second occluding device, such as, for example, one of cantilever C-arms 208-1-208-3. Cantilever C-arms 208-208-3 are deflectable relative to cartridge plate 202. The cantilever C-arm 208 has a bottom protrusion portion 207. The protrusion portion 207 includes a plateau and a ramp configured to at least partially occlude the main channel 302, as shown in FIGS. 6A and 6B, to prevent passage of the drug depots 140. The bottom protrusion 207 is flexibly disposed by virtue of the deflection of the cantilever C-arm 208 to allow passage of the drug depots 140 through the main channel 302 on application of force upon the drug depots 140 from the plunger 120.

As shown in FIGS. 5B-1-5B-3, the cantilever C-arms 208-1-208-3 have upper protrusion portions 207-1-207-3, which vary in length according to the number of drug depots 140 the cartridge plates 200-1-200-3 are intended to retain. Upper protrusion portions 207-1-207-3 each have a plateau and a ramp to permit sliding of the drug depots 140 in the main channel 302, while deflecting the cantilever C-arms 208-1-208-3. Hence, the upper protrusion portions 207-1-207-3 extend to positions proximal to the retaining panels 213 to prevent the drug depots 140 from sliding out of the main channel 302 and excessive movement of the drug depots 140 within the main channel 302. The upper protrusion portions 207-1-207-3 extend into the main channel 302 such that the ramps at least partially occlude the main channel 302 and prevent passage of the drug depots 140 there through. The ramps of the upper protrusion portions 207-1-207-3 keep the drug depots 140 within a region of the main channel 302 and the retaining panels 213 maintain the drug depots 140 within the main channel 302. Lower ends of the upper protrusion portions 207-1-207-3 are not ramped and are substantially at a right angle to the axis of the main channel 302 so as to block passage of one of drug depots 140 in an upward direction as a check valve would. In some embodiments, the lower ends of the upper protrusion portions 207-1-207-3 are rounded or ramped as a spring constant of the cantilever C-arms 208-1-208-3 is sufficient to prevent upward passage of the drug depots 140.

As discussed above, the ramped protruding portions of the protrusion portions 207-207-3 each include a ramp and a plateau. The push rod 110 is configured to push at least one of the drug depots 140 such that at least one of the drug depots 140 slides along the ramp of one of the protrusion portions 207-1-207-3 and onto the plateau of one of the protrusion portions 207-1-207-3. At least one of the drug depots 140 slides along the plateau of one of the protrusion portions 207-1-207-3 and into the main channel 302. The push rod 110 is used to move at least one of the drug depots 140 from the main channel 302 and onto the ramp of one of the protrusion portion 207. At least one of the drug depots 140 slides along the ramp of one of the protrusion portion 207 and onto the plateau of one of the protrusion portion 207. At least one of the drug depots 140 slides along the plateau of the protrusion portion 207.

In some embodiments, the drug delivery device is loaded with a selected number of the drug depots 140. Loading is affected by selecting cartridge plate 200-1-200-3 that is configured to retain the selected number of the drug depots 140. The selected number of the drug depots 140 is placed into the main channel 302 at a lower distal end of the main channel 302. The selected one of the cartridge plates 200-1-200-3 is installed onto cartridge plate 202 of the funnel body 102. The funnel body 102 is installed into a cartridge cavity of the housing 100. The cannula is secured to the housing 100. The cannula is inserted into a patient and the push rod 110 is used to advance the drug depots 140 through the main channel 302, the end channel 303 and the nipple channel 175 to implant the selected number of the drug depots 140 in the patient.

In some embodiments, the selected one of the cartridge plates 200-1-200-3 is installed onto cartridge plate 202, and the funnel body 102 is then installed into a cartridge cavity of the housing 100. The drug depots 140 may then be breached loaded into the main channel 302 via the funnel body 102.

Cannula

The cannula is designed to cause minimal physical and psychological trauma to the patient. The cannula may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. In some embodiments, the cannula may optionally include one or more tapered regions. In some embodiments, the cannula may be beveled. In some embodiments, the cannula has a tip style for accurate treatment of the patient depending on the site for implantation, such as, for example, Trephine, Cournand, Veress, Huber, Seldinger, Chiba, Francine, Bias, Crawford, deflected tips, Hustead, Lancet, or Tuohy. In some embodiments, the cannula may also be non-coring and have a sheath covering it to avoid unwanted needle sticks.

The cannula has an internal diameter that is larger than the diameter of at least part of the push rod 110 (e.g., tip, middle, etc.) of the plunger 120 to allow at least part of the plunger 120 to be slidably received within the cannula. In some embodiments, the diameter of the cannula is the same or substantially the same throughout. In some embodiments, the diameter of the cannula becomes smaller approaching the distal end of the cannula.

The dimensions of the hollow cannula, among other things, will depend on the site for implantation. For example, the width of the epidural space is only about 3-5 mm for the thoracic region and about 5-7 mm for the lumbar region. Thus, the cannula, in some embodiments, can be designed for use in these specific areas. Some examples of lengths of the cannula may include, but are not limited to, from about 50 to 150 mm in length, for example, about 65 mm for epidural pediatric use, about 89 mm for a standard adult and about 150 mm for an obese adult patient. The thickness of the cannula will also depend on the site of implantation. In some embodiments, the thickness includes, but is not limited to, from about 0.05 to about 1.655 mm. The gauge of the cannula may be the widest or smallest diameter or a diameter in between for insertion into a human or animal body. The widest diameter is typically about 14 gauge, while the smallest diameter is about 25 gauge. In some embodiments, the gauge of the cannula is about 17 gauge to about 25 gauge.

In some embodiments, at least one of the plunger 120, the cannula and the drug depot 140 include markings that indicate the location of the plunger 120 when the cannula is positioned at or near the site beneath the skin. Radiographic markers can be included on the drug depot 140 to permit the user to accurately position the drug depot 140 into the site of the patient. These radiographic markers will also permit the user to track movement and degradation of the drug depot 140 at the site over time. In such embodiments, the user may accurately position the drug depot 140 in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

Push Rod Coupling Device

In some embodiments, surrounding the opening of the proximal end of the cannula is a generally cylindrical hub having an engagement means for engaging the housing body 104. In some embodiments, the housing body 104 includes threading, tracks, clips, ribs, or projections, and the like that allow a secure connection between the housing body 104 and the proximal end of the cannula. For example, in some embodiments, the coupling device may be a luer lock connection, where the cannula has mating threads that mate with the threads disposed on or in the housing body.

Housing and Drug Cartridge Material

In some embodiments, the housing body 104 is optionally formed of any of various shapes including, but not limited to, cylindrical or round such that the housing body 104 can accept of the drug cartridge and the plunger 120. In some embodiments, the housing body 104 includes at least one side (e.g., a flat side) configured to prevent rolling of the housing body 104. In some embodiments, the housing body 104 optionally includes a truncated circular cross section with opposing flat sides.

In some embodiments, the housing body 104 includes contours to allow easy grasping of the drug delivery device during use for insertion of at least one of the drug depots 140 within a patient. In some embodiments, the housing body is angled for right and left hand users or can be generic for both hands.

In some embodiments, the housing body 104 and the drug cartridge may be comprised of any of a variety of materials, such as, for example, polyurethane, polyurea, polyether (amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics, polycarbonate, acrylonitrile butadiene or combinations thereof.

Drug Delivery Device Kit

In some embodiments, a kit is provided which may include additional parts along with the drug delivery device combined together to be used to implant the drug depot(s) 140. The kit may include the drug delivery device in a first compartment. In some embodiments, the kit includes each of the components discussed above such that a drug delivery device can be assembled having selected features due to the features or characteristics of the components selected. The second compartment may include at least one of the drug cartridges and any other instruments needed to the implant the drug depot 140 within a patient. A third compartment may include gloves, drapes, wound dressings and other procedural supplies for maintaining sterility of the implanting process, as well as an instruction booklet. A fourth compartment may include additional cannulas. Each tool may be separately packaged in a plastic pouch or tray that is radiation sterilized. A cover of the kit may include illustrations of the implanting procedure and a clear plastic cover may be placed over the compartments to maintain sterility.

In some embodiments, the kit includes a plurality of push rods, such as, for example, push rod 110 and a plurality of cannulas that have different lengths. For example, in some embodiments, the kit includes a first push rod 110 and a first cannula each having a length configured to deliver a drug depot (e.g., at least one of drug depots 140) into a petite patient, where cannula does not need to penetrate deep into the patient. In some embodiments, the kit includes a second push rod 110 and a second cannula, wherein at least one of second push rod 110 and second cannula have a length that is greater than that of first push rod 110 and/or first cannula such that second push rod 110 and second cannula are configured to deliver a drug depot (e.g., at least one of drug depots 140) into a normal patient, where second cannula needs to penetrate deeper into the patient, than with a petite patient. In some embodiments, the kit includes a third push rod 110 and a third cannula, wherein at least one of third push rod 110 and third cannula have a length that is greater than that of second push rod 110 and/or second cannula such that third push rod 110 and third cannula are configured to deliver a drug depot (e.g., at least one of drug depots 140) into an obese patient, where third cannula needs to penetrate deeper into the patient, than with a normal patient.

Method of Using the Drug Delivery Device.

A method is provided for delivering at least one drug depot, such as, for example, at least one of drug depots 140 to a site beneath the skin of a patient. In some embodiments, the method comprises assembling the drug delivery device discussed above. In some embodiments, the drug delivery device is pre-assembled and the method thus comprises using the pre-assembled drug delivery device, as discussed herein. In some embodiments, using the drug delivery devices comprises selecting a drug delivery site beneath the skin of the patient and dispensing at least one of the drug depots from the drug delivery device to the drug delivery site.

In some embodiments, the method includes using the drug delivery device for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, post-operative pain, tissue pain and pain associated with injury or repair of cervical, thoracic, and/or lumbar vertebrae or intervertebral discs, rotator cuff, articular joint, TMJ, tendons, ligaments, bone, muscles, and the like.

In some embodiments, the method includes using the drug delivery device to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings. As such, features of any of the embodiments discussed above may be incorporated into any of the other embodiments discussed above to provide a drug delivery device having selected features and characteristics.

What is claimed is:

1. A device for delivering a drug depot into a patient via a cannula for passage of said drug depot, said device comprising:
    a housing comprising opposite proximal and distal housing ends, the distal housing end having a coupling mechanism;
    a drug cartridge positioned within said housing and comprising a cartridge depot channel dimensioned to slidably expel said drug depot, said drug cartridge comprising a first occluding device that includes a ramp and a plateau each extending into the channel, the plateau extending distally from the ramp, said first occluding device at least partially occluding said cartridge depot channel at a first occluding position to prevent said drug depot from moving beyond said first occluding device, said drug cartridge further comprising an alignment boss comprising an end channel coaxial with said cartridge depot channel and distal to said first occluding device; and
    a push rod slidably receivable in said housing and said drug cartridge to move said drug depot beyond said first occluding device, into said cartridge depot channel, through said cannula and into said patient,
    wherein application of a force to said drug depot by the push rod deflects said first occluding device an amount to allow said drug depot to move beyond said first occluding device.

2. A device for delivering a drug depot according to claim 1, further comprising at least one drug depot comprising a therapeutically effective amount of a drug and a biodegradable polymer.

3. A device for delivering a drug depot according to claim 2, comprising two or three drug depots.

4. A device for delivering a drug depot according to claim 1, further comprising a second occluding device that includes a second ramp and a second plateau each extending into the channel, said second occluding device at least partially occluding said cartridge depot channel at a second occluding position to prevent said drug depot from moving beyond second occluding device, wherein application of a second force to said second occluding device by the push rod deflects said second occluding device an amount to allow said push rod to move beyond said second occluding device.

5. A device for delivering a drug depot according to claim 4, wherein said second occluding device has a length sufficient to accept a maximum of one drug depot in said cartridge depot channel between said first and second occluding devices.

6. A device for delivering a drug depot according to claim 4, wherein said second occluding device has a length sufficient to accept a maximum of two drug depots in said cartridge depot channel between said first and second occluding devices.

7. A device for delivering a drug depot according to claim 4, wherein said second occluding device has a length sufficient to accept a maximum of three drug depots in said cartridge depot channel between said first and second occluding devices.

8. A device for delivering a drug depot according to claim 1, wherein said plateau at least partially occludes said cartridge depot channel at said first occluding position.

9. A device for delivering a drug depot according to claim 1, wherein said drug cartridge comprises a cartridge body, said alignment boss extending from a distal end of said cartridge body, said cartridge body being positioned in a first portion of a cartridge cavity of said housing and said alignment boss being positioned in a second portion of said cartridge cavity, said second portion having a diameter that is less than that of said first portion.

10. A device for delivering a drug depot according to claim 1, wherein said push rod has a length that is long enough to expel a drug depot through a combined length of said housing and said cannula.

11. A device for delivering a drug depot according to claim 1, wherein:
said drug cartridge comprises a first cartridge plate and a second cartridge plate, said first cartridge plate and said second cartridge plate, in combination, defining said cartridge depot channel; and
said first and second cartridge plates comprise a cartridge engagement structure securing said first cartridge plate to said second cartridge plate and disposed between a distal cartridge end and an opposite proximate cartridge end of said drug cartridge.

12. A device for delivering a drug depot according to claim 11, wherein said cartridge engagement structure includes engaging members extending from one of said second cartridge plate and said first cartridge plate, said other one of said second cartridge plate and said first cartridge plate comprising engaging openings configured to engage said engaging members.

13. A method for delivering a drug depot, comprising:
providing a device for delivering a drug depot into a patient via a cannula for passage of said drug depot, said device comprising:
a housing comprising opposite proximal and distal housing ends, the distal housing end having a coupling mechanism,
a drug cartridge positioned within said housing and comprising a cartridge depot channel dimensioned to slidably accept said drug depot, said drug cartridge comprising a first occluding device that includes a first ramp and a first plateau, the first plateau extending distally from the first ramp, said first occluding device at least partially occluding said cartridge depot channel at a first occluding position to prevent said drug depot from moving beyond said first occluding device without force applied to said drug depot sufficient to deflect said first occluding device an amount to allow said drug depot to move beyond said first occluding device, said drug cartridge further comprising an alignment boss comprising an end channel coaxial with said cartridge depot channel and distal to said first occluding device, and
a push rod slidably receivable in said housing and said drug cartridge to move said drug depot into said cannula from said cartridge depot channel, through said cannula and into said patient;
inserting said push rod into said cartridge depot channel;
advancing said push rod to apply said force to said drug depot to deflect said first occluding device in the amount to allow said drug depot to move beyond said first occluding device; and
further advancing said push rod to expel said drug depot from said device and into said patient;
wherein said drug depot comprises multiple pellets or other solid drug forms.

14. A method for delivering a drug depot as recited in claim 13, wherein said device provided for delivering a drug depot into a patient via a cannula for passage of said drug depot further comprises a second occluding device that includes a second ramp and a second plateau, said second occluding device at least partially occluding said cartridge depot channel at a second occluding position to prevent said drug depot from moving beyond said second occluding device without force applied to said drug depot sufficient to deflect said second occluding device an amount to allow said drug depot to move beyond said second occluding device and advancing said push rod beyond said second occluding device to expel said drug depot from said device and into said patient.

15. A method for delivering a drug depot as recited in claim 14, wherein advancing said push rod comprises pushing said drug depot using said push rod such that (a) said drug depot slides along said first ramp and onto said first plateau, and (b) said drug depot slides along said first plateau and into said cannula.

16. A method for delivering a drug depot as recited in claim 14, wherein advancing said push rod comprises pushing said drug depot using said push rod such that said drug depot moves onto said first plateau from said first ramp such that said first plateau deflects to allow said drug depot to move beyond said first occluding device.

17. A kit for delivering a drug depot into a patient via a cannula for passage of said drug depot, said kit comprising:
a drug depot;
a housing comprising opposite proximal and distal housing ends, the distal housing end having a coupling mechanism;
a drug cartridge positioned within said housing and comprising a cartridge depot channel dimensioned to slidably expel said drug depot, said drug cartridge having a first occluding device that includes a ramp and a plateau each extending into the channel, the plateau extending distally from the ramp, said first occluding device at least partially occluding said cartridge depot channel at a first occluding position to prevent said drug depot from moving beyond said first occluding device, said drug cartridge further comprising an alignment boss comprising an end channel coaxial with said cartridge depot channel and distal to said first occluding device; and a push rod slidably receivable in said cartridge depot channel to move said drug depot beyond said first occluding device, through said cannula and into said patient, wherein application of a force to said drug depot by the push rod deflects said first occluding device an amount to allow said drug depot to move beyond said first occluding device.

18. A kit for delivering a drug depot according to claim 17, wherein said drug depot comprises a therapeutically effective amount of a drug and a biodegradeable polymer.

19. A kit for delivering a drug depot according to claim 17, further comprising a second push rod, said second push rod having a length that is different than that of said push rod.

20. A kit for delivering a drug depot according to claim 17, wherein the drug depot comprises two or three drug depots.

* * * * *